(12) United States Patent
Lu et al.

(10) Patent No.: US 9,684,979 B2
(45) Date of Patent: Jun. 20, 2017

(54) MRI 3D CINE IMAGING BASED ON INTERSECTING SOURCE AND ANCHOR SLICE DATA

(71) Applicant: Siemens Healthcare GmbH, Erlangen (DE)

(72) Inventors: Xiaoguang Lu, West Windsor, NJ (US); Peter Speier, Erlangen (DE); Hasan Ertan Cetingul, Cranbury, NJ (US); Marie-Pierre Jolly, Hillsborough, NJ (US); Michaela Schmidt, Uttenreuth (DE); Christoph Guetter, Lawrenceville, NJ (US); Carmel Hayes, Munich (DE); Arne Littmann, Erlangen (DE); Hui Xue, Englewood, NJ (US); Mariappan S. Nadar, Plainsboro, NJ (US); Frank Sauer, Princeton, NJ (US); Edgar Müller, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 430 days.

(21) Appl. No.: 14/299,436

(22) Filed: Jun. 9, 2014

(65) Prior Publication Data
US 2015/0091563 A1 Apr. 2, 2015

Related U.S. Application Data

(60) Provisional application No. 61/884,404, filed on Sep. 30, 2013, provisional application No. 61/990,978, filed on May 9, 2014.

(51) Int. Cl.
*G01V 3/00* (2006.01)
*G06T 11/00* (2006.01)
(Continued)

(52) U.S. Cl.
CPC ............ *G06T 11/003* (2013.01); *A61B 5/055* (2013.01); *G01R 33/4835* (2013.01);
(Continued)

(58) Field of Classification Search
USPC .......................................................... 324/309
See application file for complete search history.

(56) References Cited

U.S. PATENT DOCUMENTS

2005/0197564 A1* 9/2005 Dempsey ............... A61B 5/055
600/411
2008/0123927 A1* 5/2008 Miga ..................... G06T 7/0032
382/131
(Continued)

OTHER PUBLICATIONS

Zhang et al., "Real-time magnetic resonance imaging of normal swallowing," J Magn Reson Imaging, Jun.;35(6):1372-9 (2012).
(Continued)

*Primary Examiner* — Rodney Fuller

(57) ABSTRACT

A method of magnetic resonance (MR) imaging of a volume undergoing repetitive motion includes obtaining source slice data indicative of a plurality of source slices during the repetitive motion, and obtaining anchor slice data indicative of an anchor slice during the repetitive motion. The anchor slice intersects the plurality of source slices. The source slice data and the anchor slice data are reconstructed. A three-dimensional image assembly procedure is implemented to generate, for each phase of the repetitive motion, volume data based on a respective subset of the reconstructed source slice data. For each phase of the repetitive motion, the respective subset of slices is selected based on a correlation of the source slice data and the anchor slice data along an intersection between each source slice and the anchor slice. The source slice data of the selected subset is corrected for misalignment with the anchor slice data.

20 Claims, 11 Drawing Sheets

(51) Int. Cl.
  *A61B 5/055* (2006.01)
  *G01R 33/483* (2006.01)
  *G01R 33/563* (2006.01)
  *G01R 33/48* (2006.01)
  *G01R 33/561* (2006.01)

(52) U.S. Cl.
  CPC .... *G01R 33/56325* (2013.01); *G01R 33/4824* (2013.01); *G01R 33/5614* (2013.01)

(56) References Cited

U.S. PATENT DOCUMENTS

| | | | | |
|---|---|---|---|---|
| 2009/0115794 | A1* | 5/2009 | Fukuta | G01R 33/561 345/581 |
| 2013/0170727 | A1* | 7/2013 | Kawamura | A61B 5/7207 382/131 |
| 2015/0346300 | A1* | 12/2015 | Setsompop | G01R 33/4828 324/309 |

OTHER PUBLICATIONS

Zhou et al., "Improved vocal tract reconstruction and modeling using an image super-resolution technique," JASA 133 (6): 439-445 (Jun. 2013).

Guetter et al., "Efficient Symmetric and Inverse-Consistent Deformable Registration Through Interleaved Optimization," IEEE ISBI: 590 et seq. (2011).

Liu et al., "Regularized reconstruction using redundant Haar wavelets: A means to achieve high under-sampling factors in non-contrast-enhanced 4D MRA," Proc. Intl. Soc. Mag. Reson. Med. 20:2237 (2012).

Kellman et al., "Fully automatic, retrospective enhancement of real-time acquired cardiac cine MR images using image-based navigators and respiratory motion-corrected averaging," Magn Reson Med., 59:771-778 (2008).

Pruessmann et al., "Sense: Sensitivity encoding for fast MRI," Magn. Reson. Med., 42:952-962 (1999).

Griswold et al., "Generalized autocalibrating partially parallel acquisitions (GRAPPA)," Magn. Reson. Med., 47:1202-1210 (2002).

Boyd et. al., "Distributed Optimization and Statistical Learning via the Alternating Direction Method of Multipliers," Foundations and Trends in Machine Learning, 3(1):1-122 (2011).

Uecker et al., "Real-time MRI at a resolution of 20 ms," NMR Biomed., 23: 986-994 (2010).

Niebergall et al., "Real-time MRI of speaking at a resolution of 33 ms: undersampled radial FLASH with nonlinear inverse reconstruction," Magn Reson Med. Feb;69(2):477-85 (2013).

Zhang et al., "Real-time magnetic resonance imaging of normal swallowing," J Magn Reson Imaging, Jun;35(6):1372-9 (2012).

Rasche et al., "Continuous radial data acquisition for dynamic MRI," Magn Reson Med, 34: 754-761 (1995).

Seshamani et al., "Cascaded Slice To Volume Registration for Moving Fetal FMRI," ISBI, San Francisco, pp. 796-799 (2013).

Vuissoz et al., "Free-breathing imaging of the heart using 2D cine-GRICS (generalized reconstruction by inversion of coupled systems) with assessment of ventricular volumes and function," J Magn Reson Imaging Feb;35(2):340-51 (2012).

Xing et al., "MRI analysis of 3D normal and post-glossectomy tongue motion in speech," Biomedical Imaging (ISBI), IEEE 10th International Symposium, pp. 816-819 (2013).

\* cited by examiner

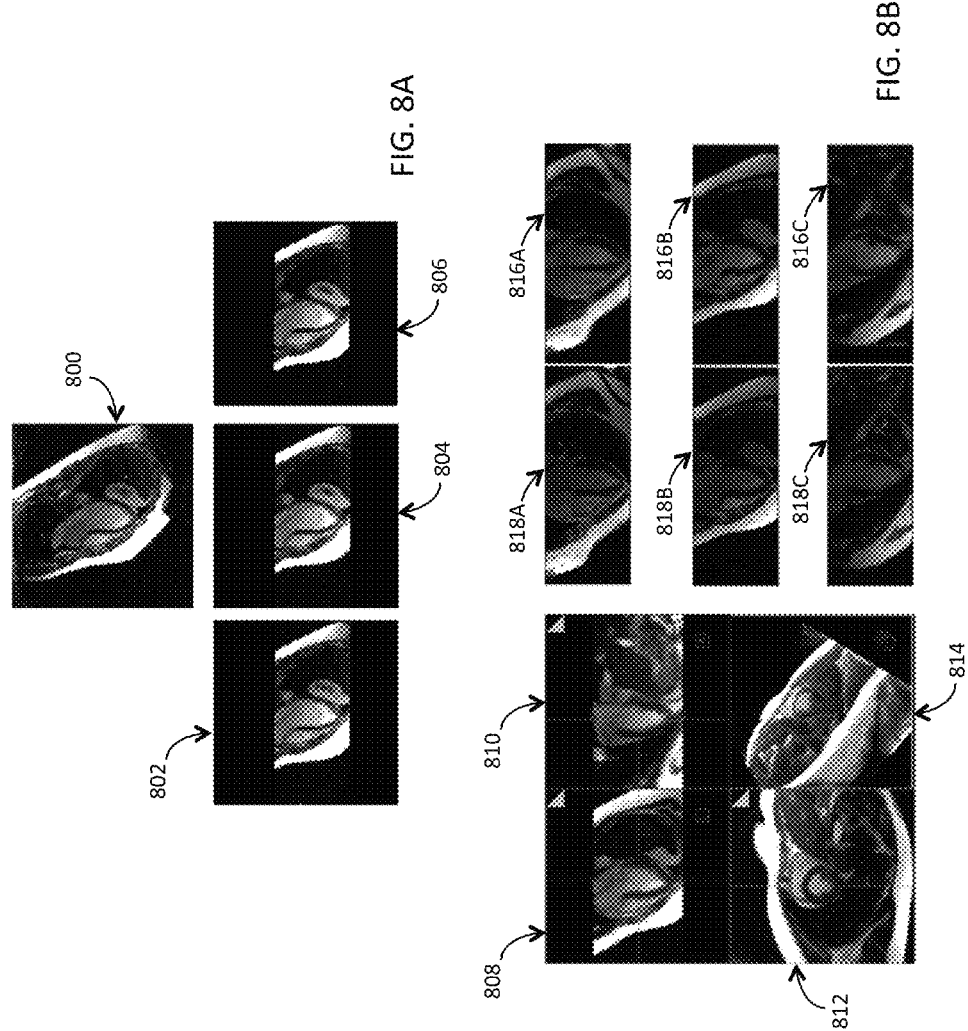

MRI 3D CINE IMAGING BASED ON INTERSECTING SOURCE AND ANCHOR SLICE DATA

CROSS-REFERENCES TO RELATED APPLICATIONS

This application claims the benefit of U.S. provisional application entitled "Method and System for Free-breathing Time-resolved 3D Reconstruction in Cardiac MRI," filed Sep. 30, 2013, and assigned Ser. No. 61/884,404, and U.S. provisional application entitled "3D Dynamic MRI Based on Assembly of 2D Images," filed May 9, 2014, and assigned Ser. No. 61/990,978, the entire disclosures of which are hereby incorporated by reference.

FIELD

The disclosure relates generally to magnetic resonance imaging (MRI) systems.

BACKGROUND

Magnetic resonance imaging (MRI) is a medical imaging technique in widespread use for viewing the structure and/or function of the human body. MRI systems provide soft-tissue contrast, such as for diagnosing soft-tissue disorders. MRI systems generally implement a two-phase method. The first phase is the excitation phase, in which a magnetic resonance signal is created in the subject with a main, polarizing magnetic field, $B_0$, and a radio frequency (RF) excitation pulse, $B_1^+$. The second phase is the acquisition phase, in which the system receives an electromagnetic signal emitted as the excited nuclei relax back into alignment with the main magnetic field after the excitation pulse $B_1$ is terminated. These two phases are repeated pair-wise to acquire enough data to construct an image.

The recovery period to allow for spin relaxation may lead to relatively slow acquisition times. The sequential nature of the scanning process also lengthens acquisition times. MR imaging accordingly often involves the acquisition of two-dimensional (2D) slices rather than three-dimensional (3D) volumes. The number of encoding steps is lower in 2D imaging, because one encoding dimension is omitted. The acquisition time for a 2D image is just a fraction of the time for a 3D image.

Newer-generation MRI systems transmit multiple radio-frequency pulse trains in parallel over independent radio-frequency transmit channels, e.g., the individual rods of a whole-body antenna. This method, referred to as "parallel transmission" or "parallel excitation," reduces acquisition times.

Reduced acquisition times and other advances enable more dynamic MRI procedures directed to studying the motion of an object. Dynamic MRI is used to provide cine imaging of the heart. The reduced acquisition times maintain image quality despite the reduced number of gradient encodings. Cardiac MR imaging is typically conducted at different planes or slices, with a separate 2D acquisition at each target plane. The heart is covered through a stack of 2D slices instead of a single 3D acquisition.

Conventional multiple-slice 2D cine acquisitions lack significant details due to large gaps between slices. The number of slices is limited by the measurement time. Moreover, misalignment of the slices arises due to extraneous motion. In cardiac imaging, artifacts may be present due to respiratory motion. Patients are asked to hold their breath repeatedly during scanning, which poses a difficult challenge for some patients.

SUMMARY

MR cine imaging is achieved for a volume undergoing repetitive motion through an assembly of source MR slice data for a plurality of source slices. A subset of source MR slice data is selected to assemble a 3D volume for each phase of the repetitive motion. The source MR slice data is selected based on anchor MR slice data. The anchor MR slice data is indicative of one or more slices that intersect the plurality of source slices.

In accordance with one aspect, a method of 3D cine MR imaging of a volume undergoing repetitive motion includes obtaining source MR slice data indicative of a plurality of source slices of the volume during the repetitive motion, obtaining anchor MR slice data indicative of an anchor slice of the volume during the repetitive motion, the anchor slice intersecting the plurality of source slices, and reconstructing, with a processor, the source MR slice data and the anchor MR slice data. Volume data is generated, with the processor, for each phase of the repetitive motion, based on a respective subset of the reconstructed source MR slice data. For each phase of the repetitive motion, generating the volume data includes selecting the respective subset of slices of the plurality of source slices based on a correlation of the reconstructed source MR slice data and the reconstructed anchor MR slice data along a respective intersection between each source slice of the plurality of source slices and the anchor slice. The reconstructed source MR slice data of the selected subset of source slices is corrected for misalignment with the reconstructed anchor MR slice data.

In accordance with another aspect, a computer program product is useful for implementing a method of 3D cine MR image reconstruction of a volume undergoing repetitive motion. The computer program product includes one or more computer-readable storage media having stored thereon instructions executable by one or more processors of a computing system to cause the computing system to perform operations. The operations include obtaining source MR slice data indicative of a stack of source slices of the volume during the repetitive motion, obtaining anchor MR slice data indicative of a plurality of anchor slices of the volume during the repetitive motion, each anchor slice of the plurality of anchor slices intersecting the stack, reconstructing the source MR slice data and the anchor MR slice data, and implementing a 3D image assembly procedure to reconstruct, for each phase of the repetitive motion, volume data based on a respective subset of the reconstructed source MR slice data. Implementing the 3D image assembly procedure includes selecting an anchor slice of a plurality of anchor slices, selecting, for each phase of the repetitive motion, the respective subset of source slices based on a correlation of the reconstructed anchor MR slice data of the selected anchor slice and the source MR slice data of each source slice of the stack along an intersection of the selected anchor slice and the respective source slice of the stack, and correcting the reconstructed source MR slice data of the selected subset of source slices for misalignment of the reconstructed source MR slice data with the reconstructed anchor MR slice data.

In accordance with yet another aspect, a data processing system is useful for an MRI system. The data processing system includes a data store in which source MR slice data and anchor slice data are stored. The source MR slice data is indicative of a plurality of source slices of the volume during the repetitive motion, and the anchor MR slice data is indicative of an anchor slice of the volume during the repetitive motion. The anchor slice intersects the plurality of source slices. The data processing system further includes a processor coupled to the data store, and configured to reconstruct, for each phase of the repetitive motion, volume data based on a respective subset of the source MR slice data. The processor is further configured to select the anchor slice from a plurality of anchor MR slices. The processor is further configured to, for each phase of the repetitive motion, select the respective subset of source slices having a maximum correlation between the source MR slice data and the anchor MR slice data along a respective intersection between each source slice of the plurality of source slices and the anchor slice. The processor is further configured to, for each phase of the repetitive motion, correct the source MR slice data of the selected subset of source slices for misalignment with the anchor MR slice data.

BRIEF DESCRIPTION OF THE DRAWINGS

FIG. 8A shows MR slice data for an exemplary anchor and source slices for the cardiac phase depicted in FIG. 4, before and after correction of the source slice.

FIG. 8B shows example orthogonal multi-planar reconstruction (MPR) images and a example 3D rendering of a volume reconstructed by the method of FIG. 2, as well as three MPR images generated from the volume.

DETAILED DESCRIPTION OF THE DRAWINGS

Figure 1:
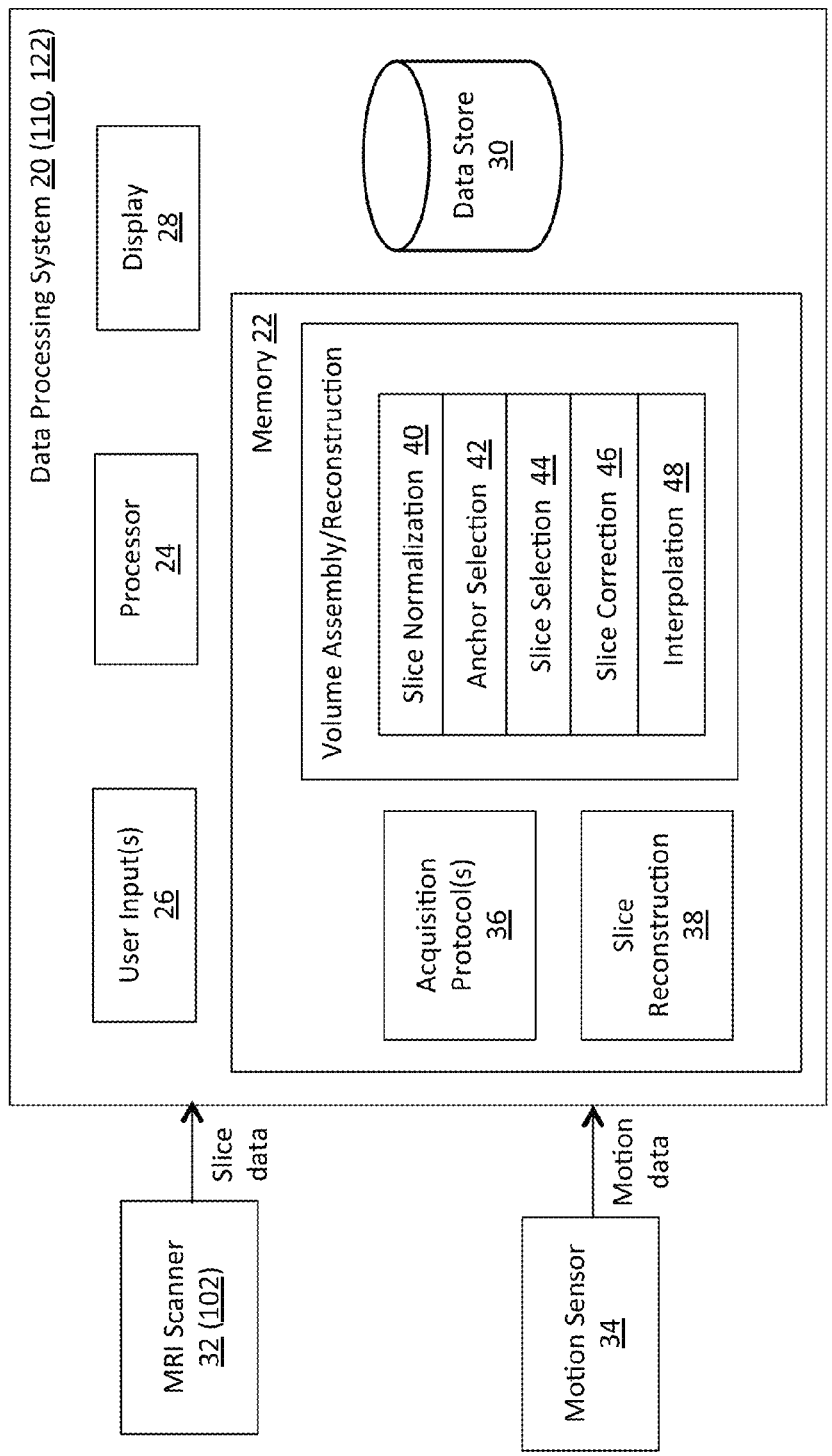
FIG. 1 is a block diagram of a data processing system to implement cine volume MRI reconstruction of an object undergoing repetitive motion in accordance with one embodiment.

Image reconstruction techniques in dynamic (or cine) magnetic resonance imaging (MRI) systems are described. The image reconstruction techniques are based on 2D slice data acquired during imaging of a volume undergoing repetitive motion. High resolution, time-resolved 3D MR images of the repetitive motion may be reconstructed from 2D slice data. The scan time for an individual slice may be short enough to effectively freeze any motion occurring during the acquisition. Data representative of the volume at a respective phase of the repetitive motion may thus be captured without motion artifacts. The disclosed embodiments may thus be used to image dynamic processes involving both the repetitive motion to be imaged as well as other, undesired motion, such as breathing motion. As a result, the slice data may be acquired while allowing the patient to breathe freely. The acquisition protocols of the disclosed embodiments may be free-breathing protocols, but breath holding may still be used. High resolution, time-resolved, volumetric data may accordingly be reconstructed while providing greater patient comfort during scanning.

The acquisition protocols of the disclosed embodiments provide source slice data for a plurality of source slices of the volume being scanned. Subsets of the source slices are selected such that misalignment is reduced or eliminated. Anchor slice data is obtained to support the selection and correction of the source slice data. The anchor slice data is representative of one or more slices that intersect the source slices of which the source slice data is representative.

With the misalignment reduced, artifacts due to other motion (e.g., non-cardiac motion, such as respiratory motion) are not present in the reconstructed images. Only data of similar motion states is selected for reconstruction. The anchor-based selection of source slices may avoid the issues presented in other MPR procedures. For example, long-axis MPR images of the heart generated from short axis acquisitions may otherwise present significant misalignment across slices due to imperfect breathing control. The misalignment may render the MPR images not clinically useful. As described below, such misalignment may be avoided through use of long axis (LX) slice data as anchor slice data for appropriate selection of short axis (SX) slice data for 3D reconstruction in accordance with the disclosed embodiments.

The source slices may be contiguous slices of the volume being imaged during repetitive motion. In some cases, the contiguous slices are a stack of slices. The source and anchor slice data sets may be acquired more quickly than a single 3D acquisition of the volume.

The coverage of the intersecting slices may correspond with the volume of interest. If the motion is contained within a fraction of the volume, the coverage of the intersecting slices may be limited to the fraction of the volume. For example, the intersecting slices may focus on the throat and mouth in speech images. The number of slices scanned may thus be minimized. Various orientations and configurations of anchor and source slices may be used.

The reconstruction techniques generate a 3D movie (3D plus time, or 3D+t image) from the slice data. The resulting 3D+t images are useful because, for instance, any desired cross-section may be created from the 3D+t data after the slice data is acquired. For example, the heart may be evaluated at any oblique plane through multiple planar reformatting without involving additional patient scanning. The 3D+t images may also provide more context information than slices alone. Such retrospective analysis is supported despite reliance on 2D scan data. The retrospective analysis is also useful because the 3D reconstruction or assembly procedure does not rely on organ or other models, but rather a 2D fluoroscopic (e.g., continuous) acquisition protocol of intersecting slices.

The reconstruction techniques are configured to address breathing motion and/or other extraneous motion. The extraneous motion may be rigid and/or non-rigid motion. The reconstruction techniques are not reliant upon interleaved navigator scans, although anchor and source slice scans may be interleaved in some cases. The anchor slice scans may differ from navigator scans relied upon in other reconstruction procedures in the sense that the roles of the source slices and anchor slices may be reversed in the disclosed embodiments. The anchor slice data may thus be alternatively used as source slice data and accordingly provide pixel or voxel contributions for the final 3D reconstructed results. The source slice data may instead be acquired as a continuous stream of real-time 2D images. Any anchor slices may then be scanned.

The acquisition protocols and reconstruction techniques of the disclosed embodiments are not reliant upon a gating signal from an external sensor. The source and anchor slices may be scanned without a trigger or other signal related to the motion cycle or phase. In some cases, external sensors are used to time stamp the slice data. But the data provided by the external sensor is not used for gating the MR acquisition protocol. Alternatively, gating or triggering is used.

The disclosed embodiments provide 3D+time cine data via reconstruction of a volume for each phase (e.g., cardiac phase) of the repetitive motion. The procedure used to reconstruct the volume for each phase includes a number of processing stages or modules. The processing stages may include various combinations of phase normalization, anchor slice selection, source slice selection based on the selected anchor slice(s), source slice correction based on the selected anchor slice(s), and interpolation to generate further volume data. Some of the processing stages may be implemented in support of multiple motion phases, while others may be implemented for each motion phase.

In some embodiments, slice data is acquired for multiple anchor slices. The anchor slices may be non-parallel, complementary slices. The anchor slice data of one or more anchor slices may then be selected for use as anchors to select and correct the source slice data. The selection of the anchor slices and selection of source slice data includes correlation analysis. Acquisition of the anchor slice data may be contiguous.

Although described in connection with cine cardiac imaging, the disclosed embodiments may be used for reconstructing other sets of 2D images of a variety of different objects that are moving in substantially periodic or repetitive patterns. For example, the disclosed embodiments may be used in connection with reconstructing images of the throat, such as speech imaging. A variety of other repetitive motions may be measured, including eye motion (blinking) and joint motion. The disclosed embodiments are accordingly not limited to cardiac magnetic resonance (CMR) imaging or any other repetitive motion. In some embodiments, information regarding the phase of the motion is gathered or obtained via an external sensor (e.g., a camera or other sensor) or via the MR slice data. In such cases, the 3D reconstruction or assembly procedure addresses other motion, such as rigid body motion (e.g., a head tilt in speech imaging) or joint displacement in joint motion imaging.

In other embodiments, information regarding the phase of the motion is not used, and the assembly procedure reconstructs data representative of the object at multiple (e.g., all) motion states. The motion states may be indicative of, and/or result from, motion in addition to the repetitive motion. For example, the additional motion may be respiratory motion or rigid body motion (e.g., patient motion). Reconstruction of multiple motion states may be useful when the additional motion has a completely different characteristic (e.g., rigid body motion) than the repetitive motion, or is otherwise separable (e.g., during assembly) from the repetitive motion. The repetitive motion and the additional motion may be separable via anchor selection, as with breathing motion in connection with cardiac imaging and/or other techniques. For example, the different motions may be separated via segmentation of structures (for rigid motion) or via application of landmark detection. A rigid transformation may then be calculated for correction. In non-rigid motion cases, a non-rigid registration with a large regularization term may be applied in a manner similar to that described below for motion correction. Still other separation techniques may rely on image-based rigid/non-rigid motion separation. The reconstruction of multiple motion states without additional sensor information using these techniques may also be used in imaging cardiac motion for multiple breathing phases, rather than for just a single breathing phase.

Repetitive processes are those dynamic processes that are periodic or substantially periodic. The motion need not be identically repetitive over all cycles. The cycles may be nearly identical or substantially similar to one another. Substantially similar may, for example, account for variation in physiological cycles, such as the cardiac cycle varying by +/−10% for a given patient. The dynamic process may be repeatable in pseudo-periodic fashion. The degree of similarity leads to a corresponding amount of artifacts in the resulting cine volume images. An acceptable deviation from identical periodicity may thus vary based on the tolerance for artifacts in a given application.

The number of repetitions of the repetitive motion to be imaged may correspond with the desired resolution of the volume being scanned. For example, the minimum number of repetitions may correspond with the smallest dimension of the volume being scanned. The number of repetitions may additionally or alternatively depend on the periodicity of the dynamic process.

Although described in connection with dynamic processes that are slow enough to be captured by real-time 2D MRI systems, the disclosed embodiments may be applied to dynamic processes having higher speeds or frequencies. If the motion of the dynamic process exceeds the image acquisition speed or update rate of the MRI scanner (for a given spatial image resolution), then components of the dynamic process in such motion may be rendered as averages. For example, in speech imaging, components moving at acoustic frequencies may be displayed as averages.

Turning now to the drawing figures, FIG. 1 depicts a data processing system 20 for an MRI system, such as the parallel imaging MRI systems having multiple coils described below in connection with FIGS. 12 and 13. The data processing system 20 may correspond with, or be implemented by, a data processing server 122 (FIG. 12) and/or a workstation 110 (FIG. 12) of the MRI system. The data processing system 20 may be integrated or correspond with any of the components described in connection with FIG. 12. In this example, the data processing system 20 includes a memory 22, a processor 24, user input(s) 26, a display 28, and a data store 30. The processor 24 is coupled to the memory 22 and the data store 30 to execute computer-executable instructions stored in the memory 22 to process slice data, such as slice scan data or k-space scan data. The processor 24 is configured by hardware and/or software to reconstruct images from the slice data. The slice data may be stored in the data store 30 and/or processed on the fly.

The processing described herein reconstructs and provides cine 3D images for rendering or visualization on the display 28. The display 28 may present multi-planar reconstruction (MPR) images, 3D plus time (3D+t) movies, or other renderings that may be manipulated in various ways, including, for instance, cross-sections. In some cases, the display 28 may be configured to display synchronized movies of multiple MPR images. The MPR images may or may not be orthogonal.

The data processing system 20 may include fewer, additional, or alternative components. For example, the data processing system 20 may be configured as a server, such as the data processing server 122 (FIG. 12), in which the user input(s) 26 and the display 28 are not included. In such cases, the data processing system 20 may be controlled by, or include, one or more client systems (not shown) in networked communication with the server of the data processing system 20. The data store 30 may be the same or different device as the memory 22.

Slice data is obtained by the data processing system 20 for a two-dimensional region over time. In cardiac and other cases, a free-breathing acquisition protocol may be used. The slice data may be received during a scan sequence, as described below. An MR scanner 32 may provide the slice data. The MR scanner 32 may be configured in accordance with the MR scanner 102 described below in connection with FIG. 12. The MR scanner 32 is configured to acquire sets of real-time MR images. A variety of real-time acquisition sequences or protocols may be implemented by the MR scanner 32. In some cases, the MR scanner 32 may be further configured to process the acquired slice data. For example, the MR scanner 32 may include a processor configured to implement 2D image reconstruction.

In the embodiment of FIG. 1, motion data is provided to the data processing system 20 by a motion sensor 34. The motion data may be indicative of motion of the object or volume undergoing repetitive motion to be captured, reconstructed, and/or rendered via the data processing system 20. The motion data may alternatively or additionally be indicative of other motion of the patient. Such other motion may be unrelated to the repetitive motion. In cardiac examples, the other motion is breathing motion. Unrelated motion may be addressed by the data processing system 20 to avoid misalignment issues in the volumetric data reconstructed by the data processing system 20. The motion sensor 34 may be or include a camera, an electrocardiograph (ECG) sensor, a respiratory belt, or other sensor or detector.

The motion data includes timing data. The motion sensor 34 and/or the data processing system 20 may include a clock to incorporate the timing data into the motion data, or otherwise provide timing data in conjunction with the sensor data. The motion data may accordingly be used to timestamp the slice data acquired by the MRI scanner 32.

MR slice data may be stored in the data store 30 after acquisition. The slice data includes both source and anchor slice data indicative of source and anchor slices of the volume undergoing the repetitive motion, respectively. The anchor slice(s) intersect the source slices. For example, the source slices may be arranged in a stack oriented orthogonally to the anchor slice(s). The anchor slices are used to select the source MR slice data to be used for 3D reconstruction. The anchor slice data may thus be used to align or otherwise correct the source slice data. Examples of slice and anchor slices are described below.

The anchor slice data may be indicative of one or more anchor slices. The anchor slices may differ spatially. Alternatively or additionally, multiple frames of anchor slice data are obtained for each spatial slice. The MRI scanner 32 may acquire anchor slice data for any number of anchor slices. The anchor slice data for one or more anchor slices may be selected for use in 3D reconstruction as described below. The anchor slice data may be acquired contiguously or continuously, with all of the anchor slices being scanned as a group before or after acquisition of the source slice data. The source slices may thus be contiguously or continuously scanned as a group without intermediate scans for the anchor MR slice data. In other embodiments, the acquisition protocol implemented by the MRI scanner 32 interleaves anchor slice scans and source slice scans. Further parameters of the acquisition protocol may vary. For example, the acquisition protocol may use interleaved-angle symmetric/asymmetric echoes with a number (e.g., 15 to 19) of views per temporal phase and a number (e.g., 10 to 20) of interleaves. Examples of anchor and slice data sets are described below in connection with FIGS. 4 and 5 (cardiac imaging) and FIGS. 9 and 10 (non-cardiac imaging).

The cine volumetric images may be reconstructed before or in parallel with storage in the data store 30. The anchor and source slice data may be previously captured or acquired by the MRI scanner 32. The anchor and source slice data may be later obtained from the data store 30 and/or a different data store. Either way, the slice data is thereafter accessible from the data store 30 for image reconstruction.

In the embodiment of FIG. 1, the memory 22 includes acquisition protocol instructions 36 to support the acquisition or examination sequence implemented by the MRI scanner 32. The acquisition protocol instructions 36 may be implemented by the processor 24 (and/or another processor) to direct the acquisition of the slice data. In other embodiments, the acquisition protocol instructions 36 are stored and/or implemented elsewhere in the MR system of FIG. 12, such as within the MRI scanner 32.

The acquisition protocol instructions 36 may be configured to determine or otherwise establish the orientation of the source and anchor slices. The source slices may be oriented along short axes of the volume being scanned. The source slices may be arranged in a stack. The anchor slices may be oriented along one or more long axes of the volume being scanned. The anchor slices may be disposed at different rotation angles around an axis (e.g., a long cardiac axis) that intersects the plurality of source slices. For example, in cardiac cases, the acquisition protocol instructions 36 may be configured to establish the position and orientation of the left ventricular (long) axis for use as the rotation axis for the anchor slice set. In alternative embodiments, the orientations and configuration of the source and anchor slices are reversed. Non-perpendicular anchor and source slices may be used.

The acquisition protocol instructions 36 may be configured to determine or otherwise establish the start and end positions of the stack of the source slices. The start and end positions may be established to cover the entire heart or other object being scanned. Alternatively, the start and end positions of the stack may be established to scan a volume that corresponds with a portion of the object. The acquisition protocol instructions 36 may also determine the temporal characteristics of the source slice scanning. For example, the instructions may specify the number of times each source slice is scanned.

The acquisition protocol instructions 36 may also be configured to determine or otherwise establish a starting orientation for the anchor slice set. Additional, fewer, or alternative acquisition protocol parameters may be established via the acquisition protocol instructions 36. For example, in some embodiments, the user input(s) 26 may be used to provide manual instructions to the data processing system 20. The manual instructions may establish one or more of the acquisition protocol parameters. Alternatively or additionally, the user input(s) 26 may provide an operator of the MRI scanner 32 to modify the parameters automatically provided via implementation of the acquisition protocol instructions 36.

The memory 22 includes slice reconstruction instructions 38 executable by the processor 24 to implement a slice or 2D reconstruction procedure on the slice data. Both the source and the anchor slice data may be reconstructed. As a result, the quality of the source and anchor slice data may be improved before implementation of the 3D reconstruction (or assembly) procedure. The 2D reconstruction method may process radial k-space data and incorporate coil sensitivity map estimation into the reconstruction formulation. In some embodiments, a compressed sensing-based iterative reconstruction method is implemented. For example, an iterative compressed sensing-based method that enforces L2-type data consistency (e.g., incorporating information about the coil sensitivity maps and Fourier transform of the k-space data into the formulation) and L1-type regularization (e.g., employing the weighted redundant Haar wavelets as the sparsifying transform) may be used. In addition, a variety of compressed sensing-based iterative image reconstruction techniques with different data consistency and/or regularization terms may be used. Different coil sensitivity estimation techniques may be useful to improve the 2D image reconstruction.

The memory 22 includes a number of instructions sets or modules directed to volume (or 3D) reconstruction. The 3D reconstruction is in addition to any slice or 2D reconstruction implemented in accordance with the slice reconstruction instructions 38. The 3D reconstruction is directed to generating or assembling volume data for each phase of the repetitive motion. The volume data is reconstructed and assembled from a respective subset of the source slice data. The subset of source slices is determined based on the anchor slice(s) as described below.

In this embodiment, the instructions for implementing the 3D reconstruction (assembly) procedure are arranged in the following five instruction sets or modules: a slice normalization module 40, an anchor selection module 42, a slice selection module 44, a slice correction module 46, and an interpolation module 48. Additional, fewer, or alternative modules or instruction sets may be included. For example, in some embodiments, the memory 22 does not include an instruction set or module for anchor selection. The slice normalization module 40 may not be used in some applications. The modules may be integrated to any desired extent. Further modules may be included if one or more aspects of the modules are addressed separately by another module.

The slice normalization module 40 includes instructions to configure the processor 24 to adjust, or normalize, the slice data to conform with one of the motion phases to be represented in the cine images. The normalization is implemented so that the slice data is representative of, and conforms to, the same set of time points within a cycle of the repetitive motion (e.g., a cardiac cycle). The normalization addresses how the MR scanner 32 has a frame acquisition rate not synchronized with the motion cycle. Before normalization, the slice data is indicative of various points within the motion cycle, the points also varying between motion cycles. After normalization, all of the slice data is indicative of one of several respective phases of the repetitive motion. In an exemplary cardiac case, the slice data for each acquired cardiac cycle is normalized to a 30 millisecond (ms) time step. Images are generated at the desired cardiac phases of the 30 ms time steps by interpolating between the slice data acquired immediately before and immediately after the desired cardiac phase. The slice normalization module 40 may be configured to implement the normalization via deformation—field-assisted or other interpolation between consecutively acquired source slices. In such cases, the deformation-based interpolation procedure generates new frames between two non-conforming motion phases using a deformation field derived from non-rigid registration across neighboring frames. Other normalization techniques may be used, including, for instance, linear interpolation between two neighboring frames.

The slice data may be time stamped to support the normalization. The time stamping may be based on the motion data from the motion sensor 34. The slice normalization module 40 may include instructions for obtaining time stamp data for the source slice data and/or the anchor slice data. The time stamp data may be provided in real time or previously acquired. The data processing system 20 may be in communication with the motion sensor 34 and/or other external sensors.

The motion sensor 34 may be an ECG acquisition system, laser scanner, stereo cameras, or other sensors or detectors. Cardiac phase information is thus assigned to the anchor and source slice data via the ECG acquisition. The sensor may be integrated to any desired extent with the MRI scanner 32 or be another component of the system 100 (FIG. 12).

The ECG (or other sensor) signal or data is not used to trigger MRI acquisition, but rather to identify the time point in a particular motion cycle at which the slice data is acquired. In other embodiments, the sensor signal or data is used to control the MR scanner 32.

In an alternative embodiment, motion phase data is assigned to the anchor and source slice data based on information extracted from the slice data. For example, the motion phase data may be assigned as set forth in Kellman et al., "Fully automatic, retrospective enhancement of real-time acquired cardiac cine MR images using image-based navigators and respiratory motion-corrected averaging," Magn Reson Med., Vol. 59, pp. 771-778 (2008). The slice data may be analyzed to assign a motion phase to the slice data. The information extracted from the slice data may be used instead of, or in addition to, the data provided by the motion sensor 34.

In some embodiments, further motion data is provided to the data processing system 20. The motion data may be indicative of extraneous motion, e.g., motion other than the repetitive motion being captured or imaged by the disclosed embodiments. For example, the slice data may be affected by extraneous motion, such as respiratory motion in cardiac cases, head motion in speech cases, and joint displacement in joint cases. Respiratory motion may be monitored by a respiratory belt or other sensor. Respiratory or other motion phase information may be assigned to the slice data. Such phase information may be used to bin anchor and/or slice data. The binning may be implemented in preparation for or otherwise in conjunction with the slice selection procedures described below. Data indicative of the extraneous motion may alternatively or additionally be extracted from the slice data.

The anchor selection module 42 includes instructions to configure the processor 24 to select or determine one or more anchor slices to be used for source slice selection and/or correction. In some cardiac examples, two anchor slices are selected. The anchor slice(s) may be selected from any number of anchor slices acquired or provided by the MRI scanner 32. The anchor slices may be orthogonal, or approximately orthogonal, to one another, such as two radial slices sharing a long or other axis through the volume being scanned.

The selection of the anchor slice(s) may be based on a correlation analysis involving the reconstructed anchor and source slice data. The correlation of the anchor and source slice data is evaluated or computed along a respective intersection between each source slice and each anchor slice. An anchor slice is then selected based on the computed correlation. For example, in a cardiac case, the anchor slice selected is the anchor slice having the most consistent slice data correlation at the intersection lines with the source slices over all cardiac phases. As described below in connection with the embodiment of FIG. 3, a set of source slices is selected for each anchor slice at which the correlation score reaches a local maximum. The anchor slice for which the set of source slices is most consistent across all phases of the repetitive motion is then selected. The selected anchor slice thus provides anchor slice data at which little or no other motion is occurring. The selected anchor slice may accordingly be used as an anchor for all motion phases (e.g., cardiac phases). The anchor slice selection may thus provide a mechanism for removing the misalignment and other undesirable effects that would otherwise result from other motion, such as breathing motion.

A second anchor slice may then be selected for use in selecting the source slices. In some cases, the selection is based on the first selected anchor slice. For example, the selection may be based on a determination of which of the remaining anchor slices is most correlated with the already selected anchor slice. An anchor correlation score may be computed between the selected anchor slice and each other anchor slice. The anchor slice with the maximum score of the computer anchor correlation scores may then be selected.

Any number of anchor slices may be selected for use in source slice selection. In cardiac and other cases in which other motion is occurring in addition to the repetitive motion to be captured, the additional anchor slices are selected such that each selected anchor slice is at or near the same breathing or other motion phase.

Other anchor slice selection techniques may be used. In some non-cardiac examples, the selection of one or more anchor slices may be random or based on other parameters or procedures. In another non-cardiac example, one or more anchor slices are selected for each motion phase. Thus, in some applications, the processor 24 is configured to repeat the selection of an anchor slice for each phase of the repetitive motion. The use of additional anchor slices at a respective motion phase may be useful. For example, the reconstruction and assembly techniques described herein may be more robust given the additional constraints provided by the multiple anchor slices for each motion phase. The selection may be based on the degree of correlation with source slice data associated with the respective motion phase. In some non-cardiac examples, an anchor slice of a plurality of anchor slices is selected based on the time stamp data. Further details regarding exemplary anchor selection techniques are provided below.

The slice selection module 44, the slice correction module 46, and the interpolation module 48 provide instructions to configure the processor 24 to implement a volume reconstruction procedure for each motion phase. The slice selection module 44 includes instructions to configure the processor 24 to compute the correlation along the intersection line between the anchor and source slices (e.g., LX anchors and SX slices, respectively). The correlation values calculated during the anchor selection may be used in the slice selection module 44. The processor 24 is further configured to select the source slices with high correlation. For example, the source slices having source slice data that form a local maximum in the correlation score are selected. The slice selection may be made within a local neighborhood, or proximity, of the anchor slices. The use of a local neighborhood may avoid wasting time processing source slice data for source slices at substantially different anatomical positions. A highly correlated subset of source slices may thus be selected for each motion phase.

In some embodiments, the correlation scores of the source slice data are computed consecutively, e.g., in the order in which the source slices are scanned. The selected source slices are later sorted by motion phase (e.g., cardiac phase). The order may be different in other cases. For example, the source slices may be sorted or binned by motion phase first, and then correlation scores are computed to select the subset of source slice data for each motion phase.

As a result of the correlation analysis, misalignment of the selected source slices at each motion phase is reduced or minimized. The misalignment may be due to other, extraneous motion. In cardiac cases, the extraneous motion may be respiratory motion. Selecting the source slices most correlated with the anchor slice(s) may thus cause the selected source slices to end up at the same or similar respiratory phase. The subset of slices selected for each cardiac phase may thus be reliably assembled into a volume that covers the heart (or other object of interest). The assembly process is then repeated for a number of cardiac phases to generate a set of volumes to depict the entire cardiac cycle.

In non-cardiac cases, the anchor correlation analysis reduces the misalignment of the source slices due to motion other than the repetitive motion being imaged. The extraneous motion may thus be indicative of motion other than respiratory motion.

The selected source slices may still exhibit some misalignment with the anchor slices. The instructions of the slice correction module 46 configure the processor 24 to correct the source slice data of the selected source slices. Correcting the source slice data leads to 3D images with a reduced number of artifacts. For each phase of the repetitive motion, the source slice data of the selected subset of source slices is corrected for misalignment with the anchor slice data. Residual misalignment between the selected source slices may be iteratively corrected through an optimization procedure. For example, the correlation with the anchor slices is optimized while constrained by neighboring source slices through a non-rigid registration procedure. One exemplary procedure may calculate, for a target slice T to be corrected, a reference slice R by interpolating between the slice above and slice below the target slice T. Then, deformation fields are computed through non-registration between slices T and R. A series of slices are then generated by interpolating the deformation fields from slices T to R. Each slice is evaluated to calculate the correlation score at the intersection with the anchor slice(s). The slice in this series with the best correlation score is used as the corrected slice in this embodiment. The non-rigid registration optimization procedure may be implemented at the 2D or slice level and/or at the 3D or volume level. For example, in some embodiments, the correction procedure includes selecting a key volume as a reference to be used in a non-rigid registration.

The selected source slices may also exhibit misalignment with neighboring slices (e.g., spatially neighboring slices). Rigid registration techniques may be implemented between neighboring slices to compensate for inconsistencies in the position of the individual slices. Alternatively or additionally, deformable registration techniques are implemented between neighboring slices to compensate for inconsistencies in the shape of the individual slices.

The interpolation module 48 includes instructions to configure the processor 25 to complete the remainder of the volume for the respective motion phase. Voxel intensities may be provided to complete the remainder of the volume. A 3D grid of intensity values may thus be provided based on the selected and corrected source slice data. In cardiac cases, voxel intensities may be interpolated to provide a regular $1.82^3$ mm$^3$ 3D grid. In some embodiments, a scattered interpolation procedure is implemented. Various procedures may be used to compound the sets of slice data into volumes for optimal resolution of the final 3D+t data. The interpolation module 48 may be configured to achieve an optimal resolution that is isotropic or near isotropic.

The memory 22 is a non-transitory computer-readable storage medium in which computer-executable instructions or instruction sets are stored for execution by the processor 24 to implement the volume reconstruction and assembly procedures of the disclosed embodiments. In the embodiment of FIG. 1, the instructions are arranged as discrete modules or instruction sets. The modules or instructions sets may be integrated to any desired extent. Additional, fewer, or alternative instruction sets or modules may be stored in the memory 22. For example, the instructions relating to anchor slice selection and source slice selection may be combined into a single module. Another module or instruction set may be stored on the memory 22 for obtaining the slice data for storage in, or access from, the data store 30.

The processor 24 may be a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 24 is a single device or multiple devices operating in serial, parallel, or separately. The processor 24 may have any number of processing cores distributed over one or more devices. For example, the disclosed procedures may be implemented by a pair of central processing units (CPUs) having a total of four processing cores. The processor 24 may be a main processor of a computer, such as a laptop or desktop computer, or may be a processor for handling some tasks in a larger system, such as in an imaging system.

The memory 22 may be a graphics processing memory, video random access memory, random access memory, system memory, cache memory, hard drive, optical media, magnetic media, flash drive, buffer, database, combinations thereof, or other now known or later developed memory device for storing data or imaging information. The memory 22 is part of an imaging system, part of a computer associated with the processor 24, part of a database, part of another system, or a standalone device.

The memory 22 may include a non-transitory computer readable storage medium storing data representing instructions executable by the programmed processor 24. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, and parallel processing, as described above. Computer-readable storage media do not include communication media for carrying waves or signals.

Additional, fewer, or different components may be provided in the data processing system 20. For example, a network or network connection may be provided, such as for networking with a medical imaging network or data archival system. Any number or type of user inputs or other user interfaces may be provided.

Figure 2:
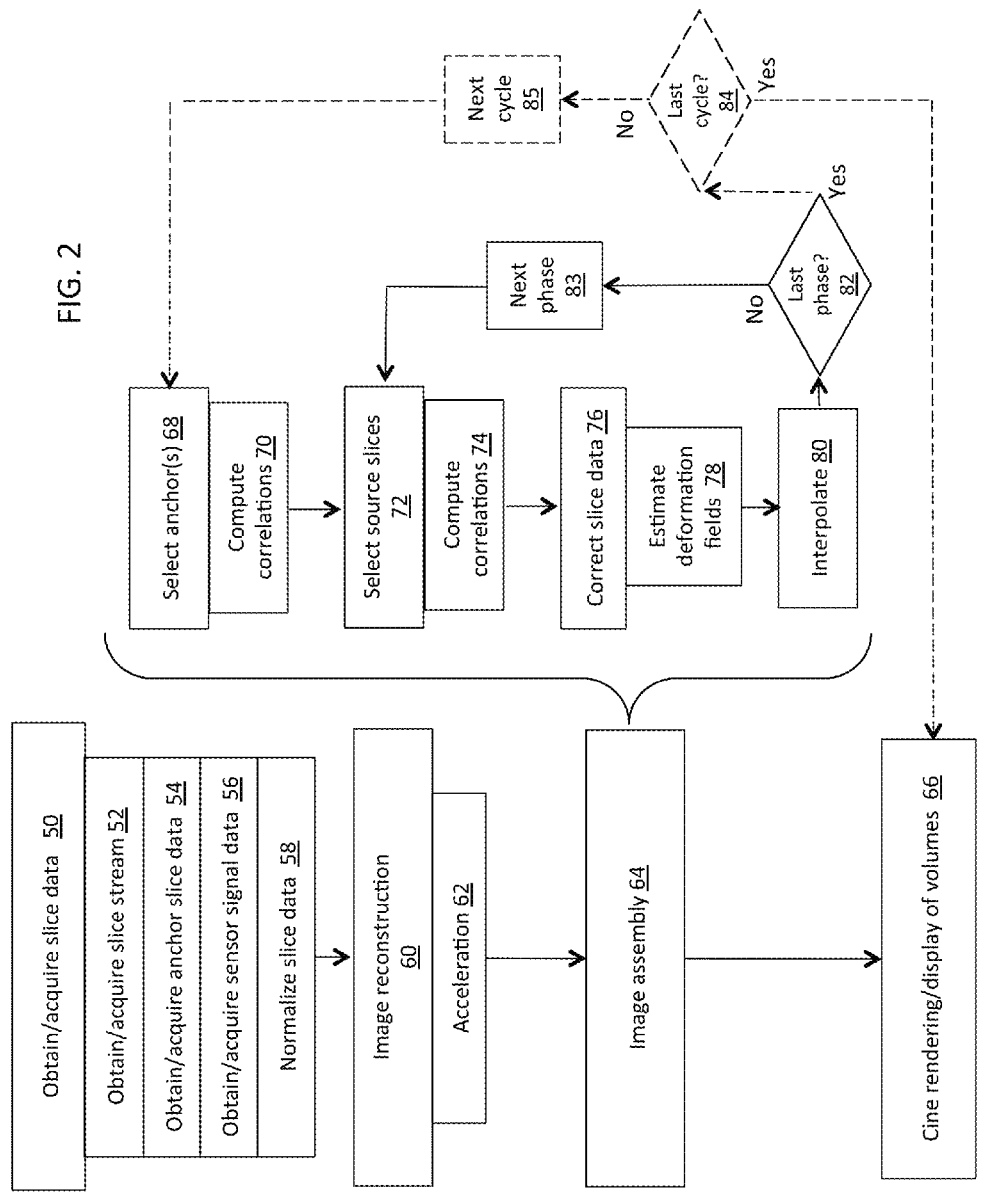
FIG. 2 is a flow diagram of one embodiment of a cine volume cine MRI reconstruction method, and that may be implemented by the data processing system of FIG. 1.

FIG. 2 depicts a method of 3D, cine, MR imaging of a volume undergoing repetitive motion. The MRI system may be configured as described above in connection with FIGS. 12 and 13. The method may be used with other MRI systems. The method includes a sequence of acts that may be performed using the processor 24 and the data processing system 20 described above in connection with FIG. 1. Other processors and processing systems may be used. Additional, fewer, or alternative acts may be included in the method. For example, the slice data may be obtained by accessing a data store, such as the data store 30 (FIG. 1), to obtain previously acquired slice data.

The method may begin in an act 50 in which slice data is acquired or otherwise obtained for a volume. The slice data includes source MR slice data (source slice data) and anchor MR slice data (anchor slice data) indicative of source slices and anchor slices of the volume, respectively, during the repetitive motion. The source slice data may be acquired or obtained for a stack of source slices scanned consecutively to provide a stream of slice data in act 52. The anchor slice data may be acquired or obtained for one or more slices that intersect the source slices in act 54. The anchor slices may also be scanned consecutively. For example, the source slices for one pass across the volume may be scanned consecutively as a group before the anchor slices are scanned as a group. Other fluoroscopic (e.g., real-time) mode acquisition sequences may be used. For example, the acquisition of the anchor slice data may be interleaved or otherwise implemented in the midst of source slice acquisition. The acts 50, 52, and 54 may include scanning the volume or accessing a data store to obtain slice data acquired during a past acquisition.

The act 50 may include acquiring or otherwise obtaining sensor signal data in act 56. The sensor signal data may include ECG data or other data. The sensor signal data may be indicative of the phase of the repetitive motion and/or indicative of other motion extraneous to the repetitive motion. The sensor signal data may be used in act 58 to normalize the slice data to conform to respective motion phases, as described above. Alternatively or additionally, the sensor signal data is used to sort the slice data into groups or bins for later assembly.

In one example involving cardiac motion, the slice data is acquired without triggering, such as ECG trigger halts, the ECG time after trigger is recorded. Therefore, in each cardiac cycle, the slice data for each slice carries a respective time stamp representative of a different cardiac phase. To reconstruct a volume at one cardiac phase, the slice data for each cardiac cycle is normalized to a pre-defined set of cardiac phases, such as 30 ms, 60 ms, 90 ms, etc. A deformation-based approach is used to interpolate a target slice ($S_T$) at a pre-defined cardiac phase with the two neighboring acquired slices, $S_a$ and $S_b$. An inverse consistent deformable registration is applied between the slices $S_a$ and $S_b$ to establish two deformation fields $D_{ab}$ and $D_{ba}$, where $D_{ab}(S_a)=S_b$, $D_{ba}(S_b)=S_a$, and where D(*) means application of the deformation field D on a slice. The deformation field for a slice includes the displacement vector for each image pixel. Then the target slice is calculated by:

$$D_{aT}=(TT_T-TT_a)/(TT_b-TT_a)*D_{ab};$$

$$D_{bT}=(TT_b-TT_T)/(TT_b-TT_a)*D_{ba};$$

$$S_T=(D_{aT}(S_a)+D_{bT}(S_b))*0.5;$$

where TT is the trigger time, S is a slice, and D is the deformation field.

The deformation-based approach captures movement of anatomical structures in the slice, while preserving the anatomical structure boundaries at the interpolated frame.

A 2D or slice reconstruction procedure may be implemented in act 60 on the anchor and source slice data. The 2D reconstruction may improve the slice data in preparation for the 3D reconstruction and volume assembly procedure of the disclosed embodiments. The slice reconstruction may include re-weighting of the k-space samples in each view for density compensation. The slice reconstruction may further include the implementation of a compressed sensing-based iterative reconstruction of the 2D images. For example, a L1 regularization based on the weighted 3D redundant Haar wavelet is applied. The dynamic images are treated as a 3D tensor and the weighted 3D wavelets are imposed for incorporating the smoothness in both spatial and temporal directions. An overlapping sliding window may be used to consider a small number of temporal phases at a time as input and estimation of the coil sensitivity maps is repeated for each window.

The reconstruction procedure may include one or more acceleration techniques implemented in act 62. A variety of acceleration techniques may be used. For example, parallel imaging techniques may be used to provide acceleration. The parallel imaging techniques may be either in the form of explicit sensitivity based methods, such as SENSE, or autocalibrating methods, such as GRAPPA. For further information on SENSE methods, please see K. P. Pruessmann et al., "SENSE: Sensitivity encoding for fast MRI," Magn. Reson. Med., 42:952-962 (1999). For further information on GRAPPA methods, please see M. A. Griswold et al., "Generalized autocalibrating partially parallel acquisitions (GRAPPA)," Magn. Reson. Med., 47:1202-1210 (2002). Additionally or alternatively, in cases having a compressed sensing-based iterative reconstruction method, the acceleration techniques include, for example, providing better initialization for the optimization problem, as well as using graphics processing unit (GPU) implementations, different solvers such as the alternating direction method of multipliers (ADMM) [S. Boyd et. al., "Distributed Optimization and Statistical Learning via the Alternating Direction Method of Multipliers," Foundations and Trends in Machine Learning, 3(1):1-122, 2011.], different regularizers (e.g., total variation norm, Tikhonov regularization), and/or computing static coil sensitivity maps rather than maps that are varying in time.

In some embodiments, the motion cycle normalization of the act 58 is implemented after the 2D slice reconstruction of the act 60.

In act 64, a 3D image assembly procedure is implemented to generate, for each phase of the repetitive motion, volume data based on a respective subset of the reconstructed source slice data. The act 64 is repeated for each phase of the repetitive motion. The volume data for each motion phase may then be displayed or rendered in act 66.

FIG. 2 provides further details regarding embodiments of the assembly procedure of the act 64. The assembly procedure may begin in act 68 with the selection of one or more anchor slices to be used in selected source slices. In some cases, a single anchor slice is selected. In other cases, the act 68 includes selecting a pair of anchor slices, which may be orthogonal to one another. The single or first anchor slice may be selected based on correlation scores computed in act 70. The correlation scores may then be evaluated to determine the anchor slice that provides the most consistent slice selection (maximum correlation) results. Further details regarding the computation of correlation scores for anchor selection are provided in connection with FIG. 3. In other cases, the anchor slice is selected based on other data, such as the motion data, or randomly selected. In still other cases, the act 68 is optional, insofar as anchor slice data is obtained for a single anchor slice.

In cardiac cases, the anchor slices may be used to reconstruct the volumes for each of the cardiac phases of the cardiac cycle. The anchor slices may be long axis slices orthogonal to, or otherwise intersecting, the short axis source slices. Use of the same anchor slice(s) to select the source slices for the entire cardiac cycle effectively excludes breathing motion and singles out the cardiac motion. Each assembled volume is accordingly disposed at the same or similar respiratory phase.

In some cases (e.g., non-cardiac cases), one or more anchor slices are selected for each phase of the repetitive motion. Correlations among candidate anchor slices may be calculated. Alternatively or additionally, the similarity of the slice selection results from each candidate anchor slice may be calculated. The use of such anchor slice data for each phase may improve assembly results. Alternatively or additionally, one or more anchor slices are selected for each cycle of the repetitive motion. For example, an anchor slice may be selected for each instance that the patient speaks a word (e.g., "blah"), blinks, moves a joint, or repeats the repetitive motion being imaged.

Once the anchor slice(s) are selected, a subset of the source slices of the plurality of source slices are selected in act 72 based on a correlation of the source slice data and the anchor slice data of the selected anchor slice(s). The subset of the source slices may be for a respective phase of the repetitive motion. The source slices may be organized or grouped by motion phase before or after the slice selection of the act 72. For example, the source slices may be grouped by motion phase in accordance with the timestamp data and/or the motion phase to which the source slice data is normalized based on the timestamp data. In the embodiment of FIG. 2, the source slices are binned by motion phase before the selection procedure for ease in illustrating the assembly of a respective volume for each motion phase.

Figure 7:
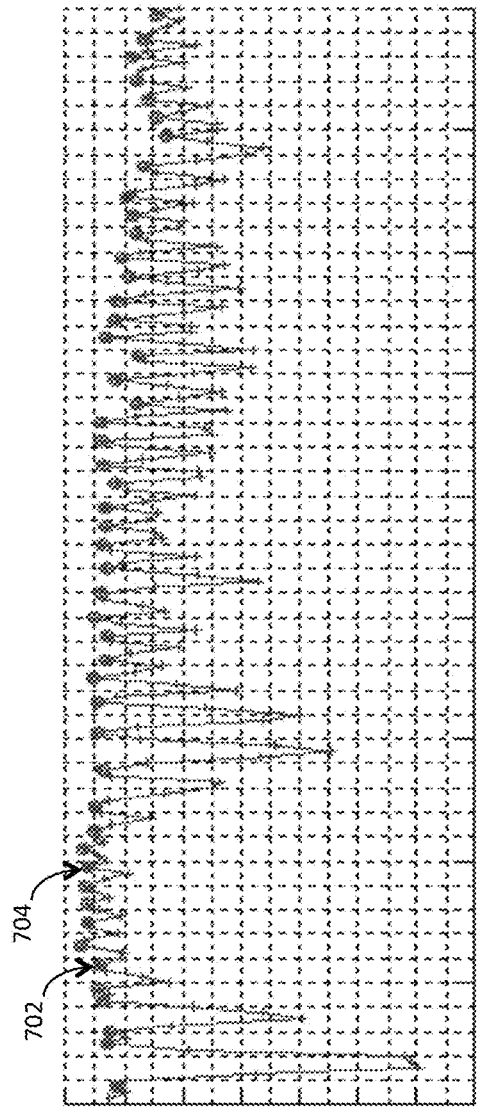
FIG. 7 is a graphical plot of correlation levels between source slice data of a plurality of source slices and anchor slice data for the exemplary cardiac phase depicted in FIG. 4 to determine select an anchor slice in accordance with one embodiment.

The correlation is computed in an act 74 along a respective intersection between each source slice and the anchor slice. The correlation of each candidate source slice with each anchor slice is computed. The source slices having locally maximum correlation scores are selected. An example of the correlation score results and slice selection is shown in FIG. 7.

Once the source slices are selected (e.g., for a particular motion phase), the source slice data is corrected in an act 76 for misalignment with the anchor slice data of the selected anchor slices. The correction may be a non-rigid slice correction. The selected source slices may still present residual misalignment due to imperfect synchronization among the source slices. The imperfect synchronization may result from various extraneous or irregular motion. For example, in cardiac cases, the extraneous motion may be indicative of a different respiratory phase. Alternatively or additionally, the extraneous motion may involve patient motion during the examination.

In some embodiments, an iterative misalignment correction process is conducted in act 78 based on non-rigid registration to estimate deformation fields. The correction process may include calculating a reference slice. The reference slice may correspond with one or more source slices selected for the volume being assembled. For example, the correction process may include calculating a reference slice $R_j^i$ for a slice $S_j^i$ to be corrected based on slice $S_{j-1}^i$ and $S_{j+1}^i$ as follows, for a given iteration I. The inverse consistent deformation field D from $S_{j-1}^i$ and $S_{j+i}^i$ is calculated as follows:

$$(D^{-1}: \text{from } S_{j+1}^i \text{ to } S_{j-1}^i);$$

$$\text{beta}=(P_j-P_{j-1})/(P_{j+1}-P_{j-1}), \text{ where } P \text{ denotes slice position; and,}$$

$$R_j^i = 0.5*(\text{beta}*D(S_{j-1}^i)+(1-\text{beta})*D^{-1}(S_{j+1}^i)).$$

The inverse consistent deformation field $D_{TR}$ may be calculated from $S_j^i$ to $R_j^i$ ($D_{TR}^{-1}$: from $R_j^i$ to $S_j^i$). The best non-rigid corrected version of $S_j^i$ is obtained by solving rho to optimize the value of the objective function defined as: Corr(rho*$D_{TR}(S_j^i)$, $LX_{anchors}$). The entire process is conducted for each selected source slice. Convergence criteria are defined as either the total deformation Sum{$D_{TR}$ of all selected SX candidates} reaches zero, or the number of iterations reaches a pre-defined maximum.

In the foregoing example, in-plane non-rigid correction is applied. The correction may thus be limited to small deformations. However, in other embodiments, a full 3D rigid and non-rigid correction process may be implemented.

In act 80, an interpolation procedure is implemented to generate a regular 3D grid for the volume assembled for each motion phase. All corrected slices may not lie on uniformly distributed positions within the volume. The interpolation procedure is accordingly applied to interpolate voxel intensities on a regular 3D grid, such as a 1.82×1.82×1.82 mm³ voxel grid. The resulting grid may thus be an isotropic volume. The interpolation procedure may be a scattered interpolation procedure.

In the embodiment of FIG. 2, the volume assembly procedure of the act 64 is repeated for each motion phase. A determination is made in decision block 82 whether the last motion phase of the motion cycle has been reached. If not, control passes to act 82 to proceed to the next motion phase, and the source slice selection, correction, and interpolation acts 72, 76, and 80 are repeated. The number of iterations may vary in other embodiments. For example, the assembly of the 3D volume data may be implemented in a single pass through the acts 68-80 in some cases.

Although depicted as a loop repeated for each motion phase, the volume assembly procedure may be implemented in other orders or sequences. For example, the volume assembly procedure may be implemented in acquisition or chronological order.

In some embodiments, the anchor slice data for the assembly is selected before implementation of the slice selection and other acts of the assembly procedure. In other embodiments, the assembly procedure of the act 64 is repeated with a new anchor slice (or new anchor slices) for a different cycle of the repetitive motion. Selection of new anchor slice data may be useful in connection with certain types of repetitive motion, such as speech motion. New anchor slice data may be selected for each instance that the patient repeats the speech (e.g., blah, blah, etc.). Control passes to a decision block 84 once the volume is assembled for the last motion phase. If slice data is available for an additional motion cycle, then control passes to act 85 in which the anchor and source slice data is obtained for the next motion cycle. Anchor slice selection in the act 68 is then implemented again. The remainder of the volume assembly procedure is then repeated with the new anchor slice data.

The method of FIG. 2 may include additional acts. For example, the volume data generated for each motion phase via the assembly process may be further processed for 3D motion correction. For example, 3D motion correction may be applied across cardiac phases. After all volumes are reconstructed at all cardiac phases, a complete motion sequence may be constructed. The above-described anchor selection and slice selection are directed to reducing motion artifacts across cardiac phases. A 3D motion correction process may be applied if the volume sequence still presents residual motion artifacts. Various 3D motion correction procedures may be used. In one embodiment, a key frame (volume) is selected as a reference. To select the reference, for each frame $F_i$, a 3D non-rigid registration is applied between $F_i$ and all other frames. The total deformation is calculated for frame $F_i$. The key frame is selected as the frame with the least total deformations. Then registration is conducted with a larger regularization constraint between the key frame and each of the other frames. The large regularization constraint captures more global motion than local constraints. The resulting volume sequence is 3D motion corrected.

Figure 3:
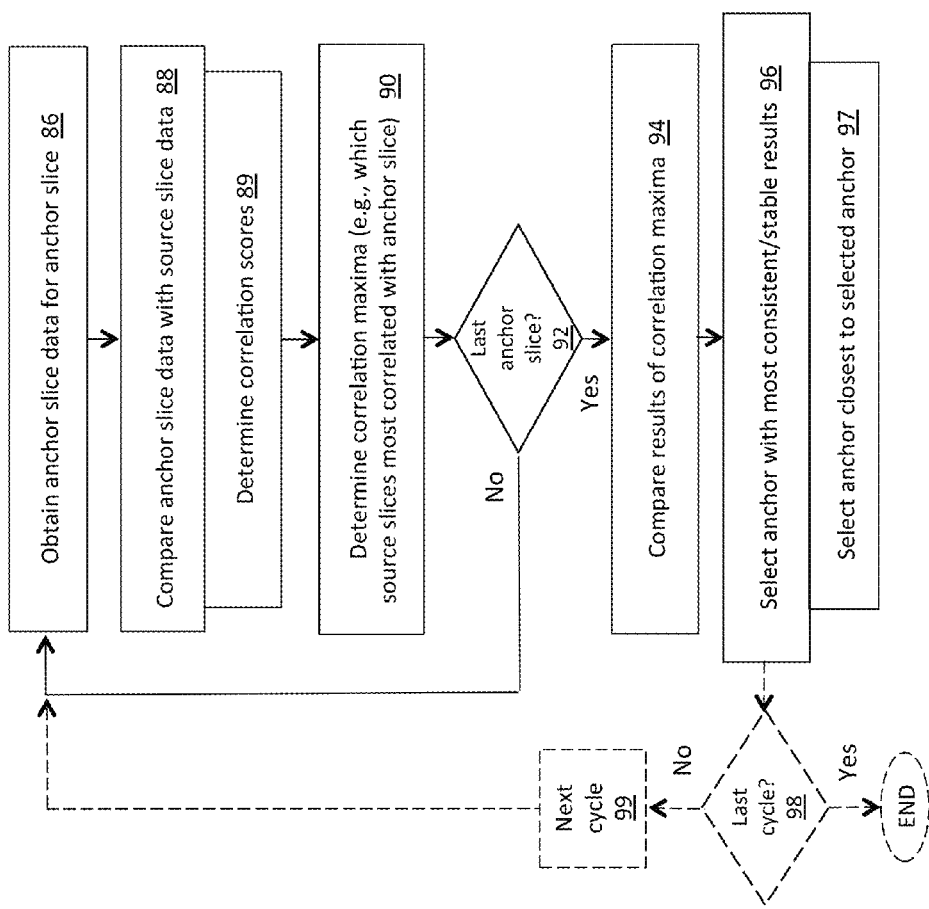
FIG. 3 is a flow diagram of an anchor slice selection procedure of the MRI reconstruction method of FIG. 2 in accordance with one or more embodiments.

FIG. 3 depicts an anchor selection procedure in accordance with one or more embodiments. In some cases, the anchor selection process is applicable to all source slice data collected over multiple repetition cycles. In other cases, the anchor selection process is repeated to select anchor slice data for each cycle. In either case, one or more anchor slices may be selected.

Figure 6:
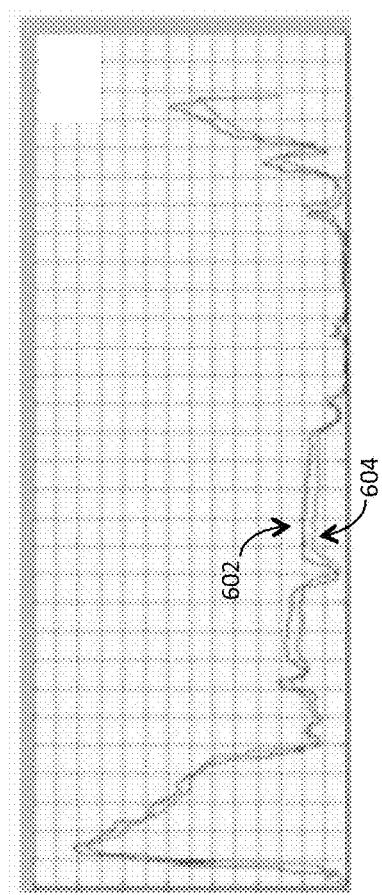
FIG. 6 is a graphical plot of a correlation between the source and anchor slices of FIG. 5 computed in accordance with one embodiment.

The anchor selection procedure may begin in an act 86 in which anchor slice data is obtained for a first anchor slice. The anchor slice data is then compared in an act 88 with the source slice data. The comparison may include computation of a normalized correlation score in an act 89 between the anchor slice and each source slice as shown in FIG. 6. For each anchor slice, all local maxima in the corresponding source slice correlation scores are selected as a set in an act 90. The local maxima in the correlation scores are indicative of which source slices are most correlated with the anchor slice. An example of the local maxima determination is shown in FIG. 7. The set selection is conducted over all motion phases. A decision block 92 determines whether the last anchor slice has been reached. If any additional anchor slices remain to be processed, then control returns to the act 86.

In act 94, a comparison of the anchor slice correlation results is conducted. The sets of source slices having the correlation score maxima are compared. The anchor slice with the most consistent source slice selection sets is selected as the anchor slice in an act 96. The source slice selection sets are those subsets of the source slices selected for each motion phase for assembly of the volume. A simplified example follows. The results for anchor slice A are source slices 1, 3, and 4 for motion phase X, and source slices 1, 2, and 3 for motion phase Y. The results for anchor slice B are source slices 2, 5, and 6 for motion phase X, and source slices 2, 5, and 6 for motion phase Y. In this example, the anchor slice B is then selected because the two subsets of source slices are the most consistent. In that simplified example, the subsets are in fact identical. In a non-simplified case, consistency may be defined as an edit distance among all pairs of selected source slice sets, where each selected source slice set is considered as a string with each element being the slice index. For example, the edit distance may be the Levenshtein distance. The edit distance may be calculated through standard dynamic programming between the two strings.

Selection of the most consistent anchor slice may improve the alignment of the source slices to be selected. For example, in cardiac cases, use of the most consistent anchor slice may direct the source selection procedure to select source slices disposed at or near the same breathing phase. In practice, the anchor slice selected for use may end up positioned at the end of inspiration or expiration (e.g., the extremities of the breathing cycle), as those points in the breathing cycle are most stable. On the other hand, anchor slices acquired during the slope of the breathing cycle are more likely to produce the most unstable or inaccurate results due to the dynamic nature of the motion cycle at those times. Despite these recognitions, the selection of the most consistent anchor slice is not based on an explicit selection of the breathing phase. However, in other embodiments (e.g., non-cardiac cases), motion data may be used to select the anchor slice.

In the embodiment of FIG. 3, an additional anchor slice may be selected in an act 97. Once the first anchor slice is selected, the first anchor slice may be used to select an additional anchor slice. For example, the additional anchor slice may be the anchor slice having the best correlation score with the first selected anchor slice. The correlation score may be computed along an intersection or overlap between the two anchor slices. The intersection may be, for example, the center longitudinal axis for the anchor slice scan sequence.

In some cases, such as non-cardiac applications, one or more additional anchor slices are selected for each motion cycle or each phase. A decision block 98 determines whether the last motion cycle has been reached. If not, the next motion cycle is selected in an act 99, and control returns to the act 86 to obtain the corresponding anchor slice data and source slice data.

Figure 4:
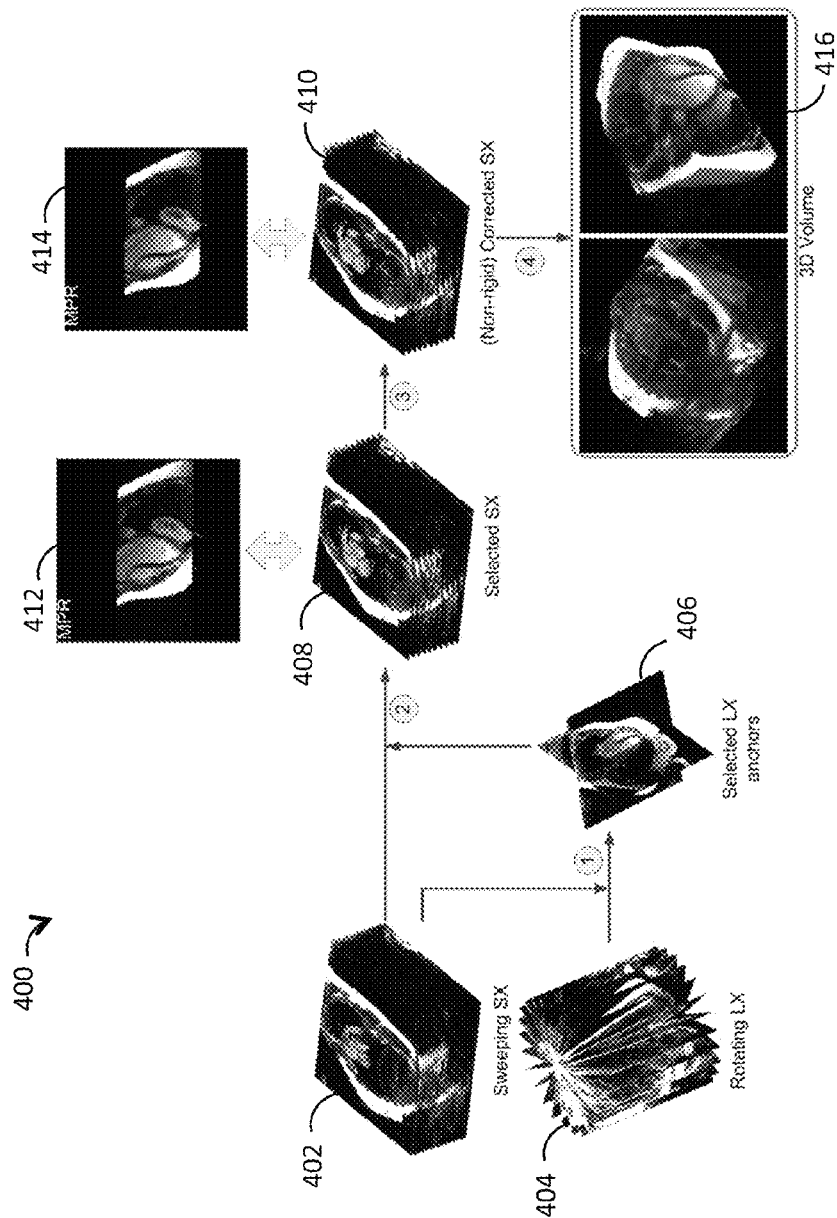
FIG. 4 is a flow diagram of a 3D reconstruction procedure of the MRI reconstruction method of FIG. 2 for an exemplary single cardiac phase in accordance with one embodiment.

FIG. 4 provides further details regarding application of the disclosed embodiments in connection with imaging cardiac motion. FIG. 4 shows a volume reconstruction workflow 400 for one cardiac phase. Some or all of the acts may then be repeated to reconstruct other volumes for the other phases of the cardiac cycle. For example, the selection of long axis (LX) anchor slices may not be repeated for the other cardiac phases. Instead, the LX anchor slices are selected for the entire cardiac cycle in an effort to exclude respiratory motion from the reconstructed volumes. Each volume may thus be at or near the same respiratory phase.

In the embodiment of FIG. 4, the source slices are a stack 402 of short axis (SX) slices. The source slices are aligned with one another as shown. The LX anchor slices are a set 404 of slices with different rotation angles around the long axis of the heart. The long axis is orthogonal to, or otherwise intersects, the stack 402 of source slices. The anchor slices are not aligned or parallel with one another.

The slice data for the stack 402 of SX source slices is acquired consecutively as a group. The set 404 of LX anchor slices are also acquired consecutively as a group. Other acquisition sequences involving, for instance, interleaving the SX and LX slices, may be used. The parameters of the acquisition sequences may vary. For example, undersampling schemes using multiple coils may be used. Full, asymmetric, or half echo radial acquisition protocols may alternatively or additionally be used. The acquisition may be free running relative to the cardiac cycle, or alternatively synchronized to the heart beat.

The SX source slices may have a small enough temporal footprint to allow the source slices to be acquired while the heart and breathing motion is effectively fixed. The slice acquisition may thus be considered to provide real-time, unsegmented, cine imaging. The slice acquisition is thus not constrained by the patient holding his or her breath. The acquisition protocol may include interleaved-angle radial sampling of the k-space tuned to maximize the image frame rate, while maintaining sufficient image quality. Total acquisition time may thus be minimized to prevent or reduce slice shift and rotation from introducing strong inconsistencies in the resulting images. Notwithstanding the foregoing, in an alternative embodiment, the source slices are oriented along the long axis, and the anchor slices having rotation angles around the short axis of the heart.

The stack 402 of source slices may be acquired using the same in-plane coordinate system for all slice scans, resulting in constant image row and column vectors in the series. For the set 404 of rotating LX anchor slices, the acquisition may include one in-plane vector (e.g., the nominal phase encoding direction) chosen to be parallel to the rotation axis. In addition, in order to avoid image quality problems due to eddy currents, the signs of the imaging gradients may be adjusted to avoid gradient inversions between adjacent images, thus keeping gradient changes between images small.

The slice acquisition may include a pre-acquisition planning stage in which the heart location and orientation are estimated. In one example, the SX sweeping stack 402 is acquired with an inter-slice distance of 0.05 mm and a slice thickness of 7 mm. The whole heart may be covered from apex to aortic arch. The LX anchor set 404 is acquired by rotating around an axis determined at the planning stage. In the example of FIG. 4, the axis is the symmetry (long) axis of the left ventricle, the angle between two contiguous anchor slices is 0.1 degrees, and each anchor slice is acquired at a 50 ms interval.

In the example of FIG. 4, the free-breathing scans were acquired with a fluoroscopic radial balanced steady-state free precession (bSSFP) sequence, an image rate 40-50 ms, and a resolution of (1.82×1.82×7) mm³. An ECG time-after-trigger signal was recorded for retrospective mapping to cardiac phases. Volume coverage was achieved by changing the scan plane position or orientation between images slightly in order to not disturb the spin steady state. The 2D slice data was processed via a 2D reconstruction procedure configured in accordance with a compressed sensing algorithm based on the teachings of Liu J et. al., ISMRM, Melbourne, Australia, 2012, p. 4249.

The acquisition protocol used interleaved-angle symmetric/asymmetric echoes with 15-19 views per temporal phase and 10-20 interleaves (in ascending order or in itself twice interleaved). The number of interleaves is selected such that (1) the total number of views (15×10 up to 19×20) is large enough to calculate faithful coil sensitivity maps, and (2) the total acquisition time is short enough so that slice shift and rotation does not introduce strong inconsistencies in the data leading to artifacts in the coil sensitivity maps. Interleaving may be used to reduce artifacts due to image inconsistency.

In an asymmetric echo, the outer part of one side of the view is omitted because signals from the outer parts of k-space connected by point symmetry have complex conjugate symmetry. That is, the outer parts are redundant. The use of an asymmetric echo reduces echo acquisition duration, and hence the sequence is faster and, for a constant image frame rate, may be used to increase the number of views per frame. In some cases, the use of an asymmetric echo also stabilizes the sequence against static field inhomogeneities and flow artifacts as the RF pulse spacing is shortened.

In 2D radial imaging, the data density in k-space is proportional to 1/r with r being the distance to k-space center. If the views are distributed over 360°, then (for a large number of views) the data density is still a function of r only (and not of the azimuth). With asymmetric echoes, the radial density changes in a step wise fashion. In the central symmetric part, the radial density is 1/r. In the outer asymmetric part, the radial density drops by a factor of two. To avoid artifacts due to the sudden density step, the measured data is reweighted by a density compensation function (e.g., a linear ramp around the step).

In the example of FIG. 4, there are 180 and 140 cardiac cycles acquired in SX and LX sets, respectively. Therefore, at each cardiac phase, there are 180 SX slices and 140 LX slices. A volume is assembled for each phase of the cardiac cycle from these SX source slices using the LX slices as anchors.

After 2D reconstruction and slice normalization to the cardiac cycle as described above, two LX anchors 406 are selected and then used for selection of a subset 408 of the SX source slices for the cardiac phase being assembled. A slice correction procedure is then implemented to generate a corrected set 410 of the SX source slices. MPR views 412 and 414 of the uncorrected subset 408 and the corrected set 410 of SX source slices are shown for comparison. Using an interpolation (or compounding) procedure, a 3D volume is generated from the corrected set 410 of SX source slices. A rendering 416 of the 3D volume and a cross-sectional view thereof may then be generated as shown. The slice selection, slice correction, and interpolation procedures are accordingly repeated for the other cardiac phases.

Figure 5:
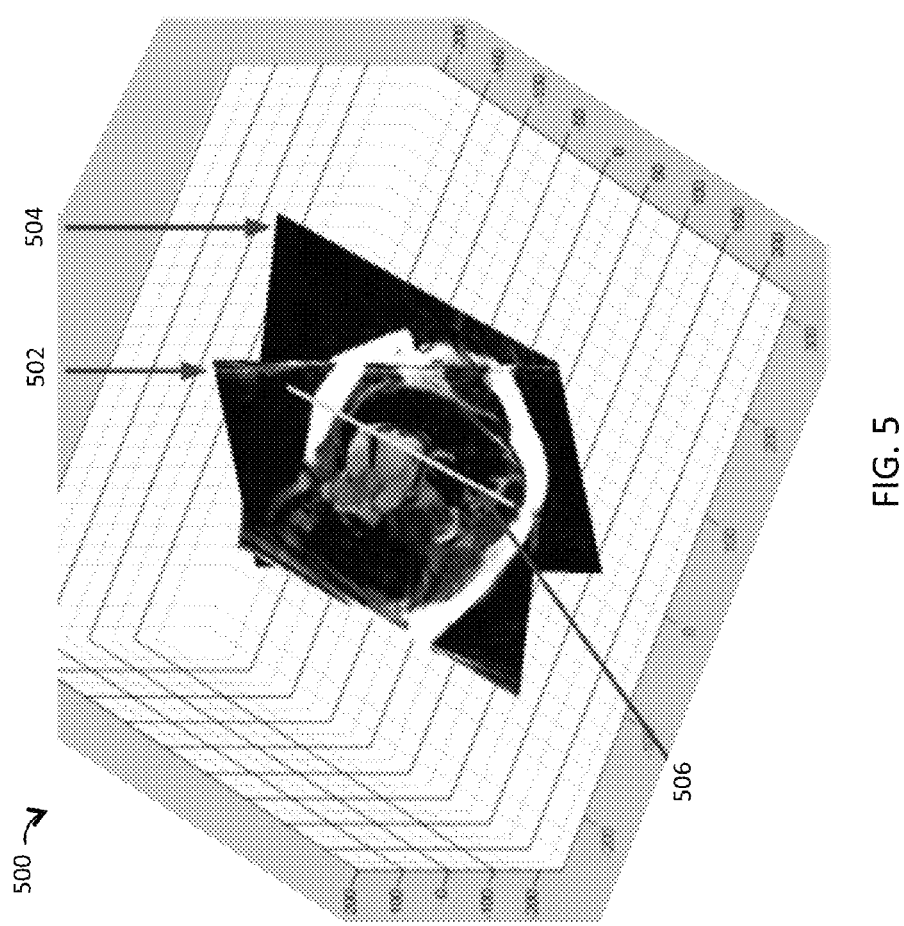
FIG. 5 depicts an example intersection of source and anchor slices for reconstructing the cardiac phase depicted in FIG. 4 in accordance with the reconstruction method of FIG. 2.

FIG. 5 is a graphical and perspective view 500 of an exemplary correlation of a respective source slice 502 and a given anchor slice 504. The correlation score is computed for an intersection 506 between the source slice 502 and the anchor slice 504. The source and anchor slices 502, 504 may have previously been normalized as described above. The correlation score is computed based on a comparison of pixel intensity signals along the intersection 506. Intensity signal values 602, 604 are plotted as a function of position for the source and anchor slices 502, 504, respectively, in FIG. 6. A correlation score may be computed from the pixel intensity comparison as described above. The correlation scores may be normalized. Scores other than the normalized cross correlation may be calculated in other embodiments.

As shown in FIG. 7, the correlation scores for each of the source slices are then compared to determine a set of source slices for the anchor slice being processed. In this example, the comparison includes determining local maxima of the correlation scores. The correlation score for each source slice is indicated with a cross shape in the plot. The correlation scores at the local maxima are circled, two examples of which are indicated with reference numerals 702, 704. The corresponding source slices are selected as a set for use in determining which anchor slice has the most consistent source slice selection sets.

FIGS. 8A and 8B show the intermediate and end results of the assembly procedure. In FIG. 8A, a selected anchor slice 800 is shown with an exemplary source slice 802 selected based thereon. Images 804, 806 are renderings of the source slice 802 after one iteration and 25 iterations of the slice correction procedure, respectively.

FIG. 8B shows three orthogonal MPR images 808, 810, 812 and a 3D rendering 814 resulting from the assembly of the selected source slices. FIG. 8B also shows three MPR images 816A-816C generated from the reconstructed volumes alongside acquired slice images 818A-818C acquired at the same views.

Figure 10:
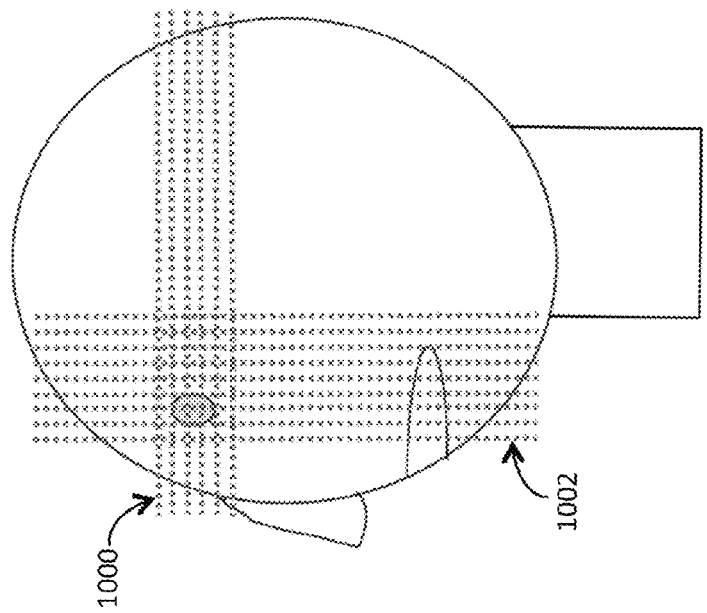
FIG. 10 is a schematic representation of source and anchor slices for cine volume reconstruction of eye motion in accordance with one embodiment.
Figure 9:
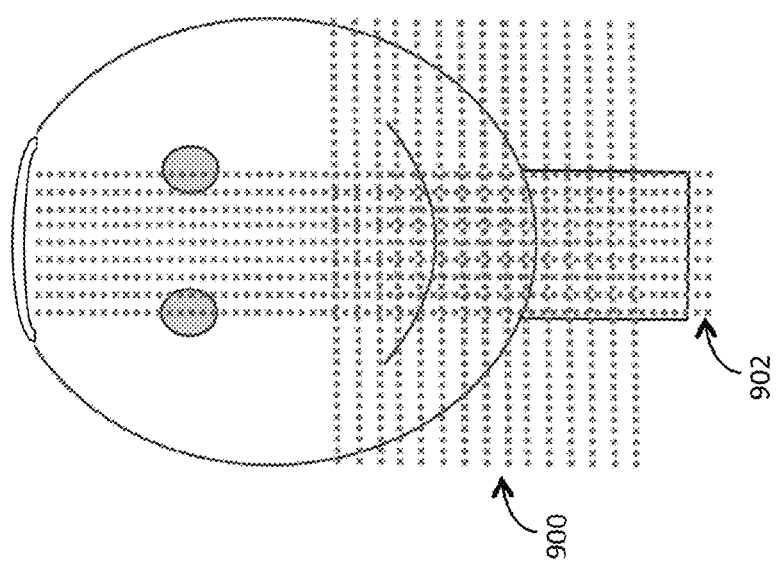
FIG. 9 is a schematic representation of short axis source slices and long axis anchor slices for cine volume reconstruction of speaking motion in accordance with one embodiment.

FIGS. 9 and 10 show exemplary source and anchor slice sets for reconstructing cine 3D volume images for other types of repetitive motion. In each case, the source and anchor slice sets are orthogonal stacks. The sets may intersect one another non-orthogonally. In FIG. 9, a set 900 of SX source slices and a set 902 of LX anchor slices are acquired to capture the repetitive motion of speech, swallowing, or other motion of the throat. The roles of the sets 900, 902 may be reversed in other embodiments. In FIG. 10, a set 1000 of lateral source slices and a set 1002 of vertical anchor slices are acquired to capture the repetitive motion of an eye blink. Either one of the sets may serve as the anchor slices or source slices. In another non-cardiac example, sets of intersecting slices are acquired during repetitive motion of a joint, such as a patient knee.

Given the intersecting sets of slices of FIGS. 9 and 10, selection of anchor slices to be used in the assembly procedure may proceed as described above. Slices from either stack may be evaluated for anchor selection. In these non-cardiac embodiments, a series of consecutive anchors may be selected to cover one repetition of the dynamic motion. Each selected anchor slice corresponds to a respective phase of the dynamic motion. Each selected anchor slice is then used to reconstruct a respective, consistent volume by selecting and aligning slices from the other stack (the source slice stack). The reconstruction of each respective 3D volume provides a sequence representing the anatomical dynamic motion cycle.

Further details of the application of the assembly procedure to a non-cardiac case are provided in connection with a speech imaging example. The patient repeatedly pronounces 'blah' while the two stacks of slices are acquired. The stacks may provide quasi-continuous coverage. As shown in FIG. 9, one stack has a sagittal (SAG) orientation, and the other stack has an axial (TRA) orientation. A fluoroscopic 2D radial bSSFP sequence is implemented with compressed sensing 2D reconstruction. In one example, the flip angle is 45 degrees, the frame rate is 27 Hz, the resolution is 1.82×1.82×7 mm$^3$, the slice shift is 0.05 mm/frame, and the inter-slice distance between source slices is 2.20±0.52 mm. These parameters of the acquisition sequence may vary. For example, a GRE sequence may be used in which the frame rate is 20 Hz, the resolution is 1.56×1.56×1.56 mm$^3$ and the inter-slice distance between source slices is 2.6±1.7 mm.

A time series of volumes is reconstructed according to the set of consecutive anchors as follows. From the SAG acquisition, a set of consecutive slices are selected as the anchor slices. The anchor slices are located around the middle line of the face and cover one repetition (cycle) of the speech paradigm. Normalized correlation was calculated for each TRA slice at the intersection line segment with the SAG anchor slice. The algorithm selected the TRA slices that were best correlated with the SAG anchor slice within a small temporal neighborhood corresponding to the average duration of the speech paradigm. Residual misalignment among selected TRA slices was iteratively corrected through non-rigid registration, thereby optimizing the correlation with the SAG anchor slice. The deformations applied during optimization were constrained by the neighboring selected TRA slices. A 3D volume was obtained by applying scattered interpolation onto an isotropic grid based on the corrected TRA slices.

Figure 11:
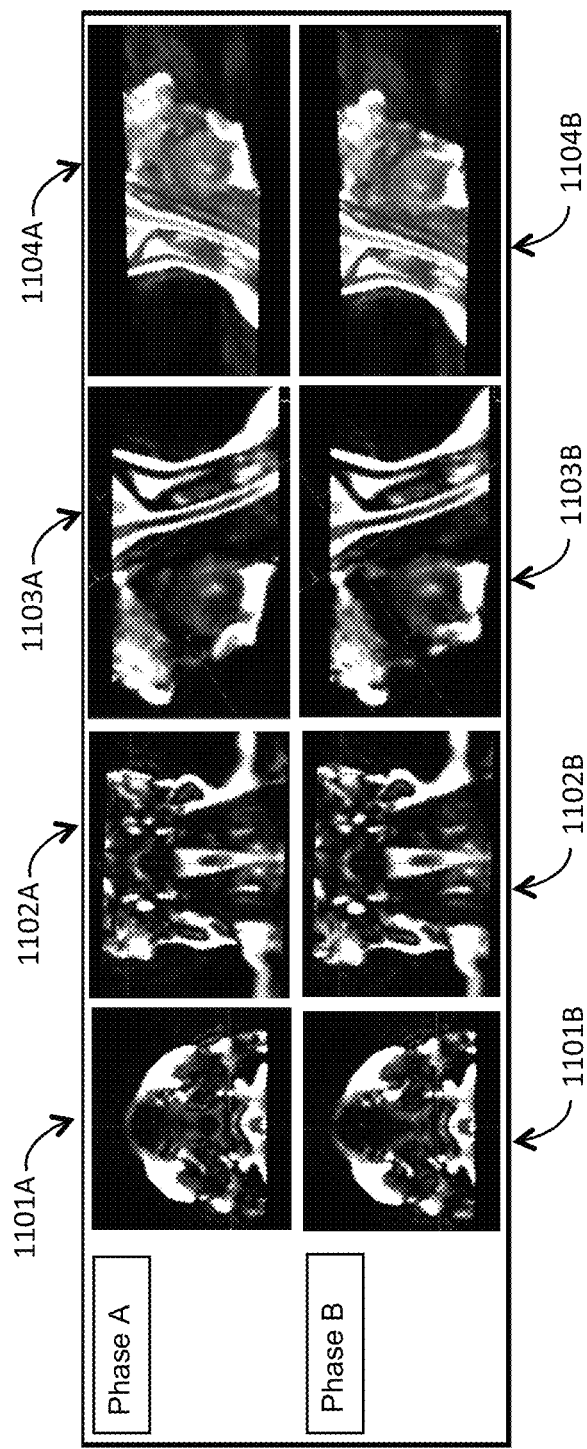
FIG. 11 depicts example images reconstructed for two phases of speech motion with the reconstruction method of FIG. 2.

FIG. 11 shows MPR images of the reconstructed volume sequence at two different speech phases A and B. For each phase, three MPR images 1101A-1103A, 1101B-1103B and one 3D rendering of the volume 1104A, 1104B are shown. Window levels are adjusted to highlight tongue and structures surrounding the vocal tract.

The experimental results demonstrate that the proposed method is capable of reconstructing consistent 3D freeze frames of the speech dynamics, capturing the dynamics (such as tongue, jaw, etc.) in 3D and in correspondence to the speech pattern (e.g., "blah") with a good balance between spatial and temporal resolution. The reconstructed image quality may be improved by tailoring the acquisition and reconstruction parameters to the specific application. Super-resolution algorithms may alternatively or additionally be applied for further improvements.

To increase the spatial resolution in the slice normal direction, the assembly procedure may also be applied to reconstruct a volume sequence from the SAG slices using the TRA slices as anchors. Both volume sequences reconstructed from the SAG and TRA slices may then be combined to generate a single volume sequence with an improved spatial resolution. For example, the volumes may be combined through scattered interpolation. For each specific application, the acquisition protocols may be adjusted to reach an optimal solution.

Figure 12:
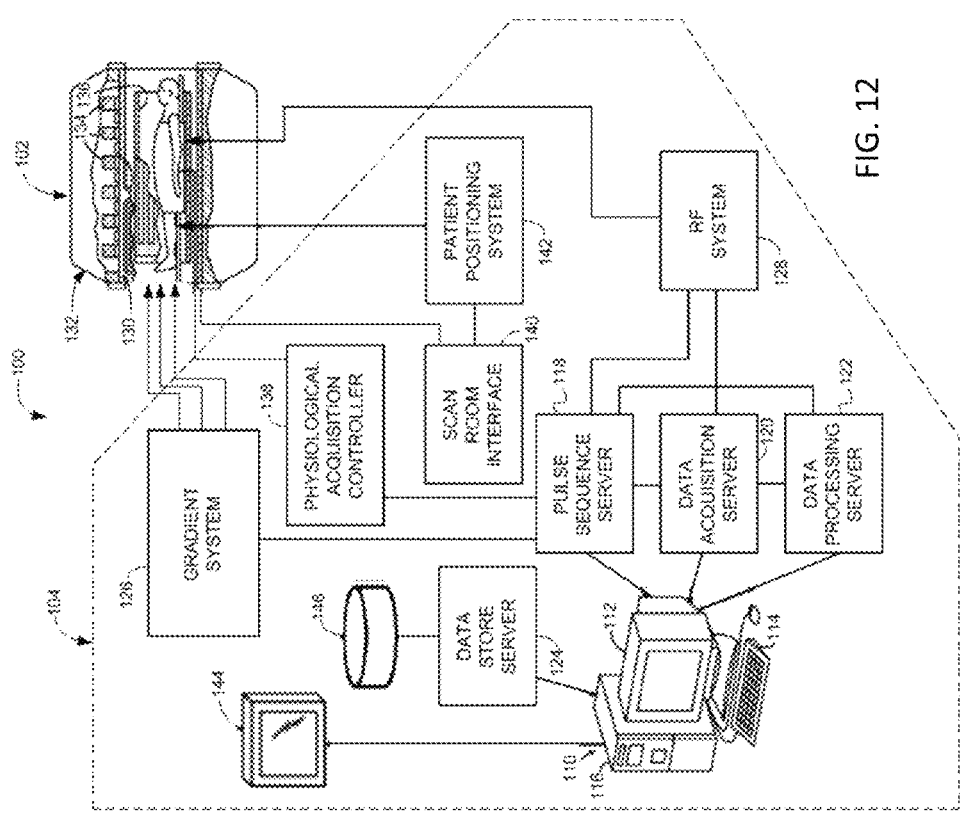
FIG. 12 is a block diagram of an MRI system that may be configured to implement the reconstruction method of FIG. 2 in accordance with one embodiment.

FIG. 12 depicts a magnetic resonance imaging ("MRI") system 100 that may be used in connection with the above-described embodiments. The MRI system 100 generally includes a scanner or data acquisition unit 102 and a control system 104 for directing the operation of the scanner 102. In an excitation phase of operation, the data acquisition unit 102 creates a magnetic resonance signal by subjecting a subject to a main magnetic field, $B_0$, to align the individual magnetic moments, or spins, of the nuclei in the tissue with the axis of the polarizing field (conventionally, the z-axis). The main magnetic field also causes the magnetic moments to resonantly precess about the axis at their characteristic Larmor frequency. The data acquisition unit 102 then subjects the tissue to an RF excitation pulse, $B_1$, with a frequency near the Larmor frequency, so that a magnetic field in the x-y plane re-orients, flips, or tips the net aligned moment, $M_z$, into or toward the x-y plane, producing a net transverse magnetic moment $M_{xy}$, the so-called spin magnetization. The excitation phase is generally tailored to localize the excitation pulse to a specific region within the subject, such as a 2D slice. In a subsequent acquisition phase of operation, the data acquisition unit 102 encodes the localized region in-plane for the slice. The region to be imaged may be scanned by a sequence of measurement cycles in which magnetic field gradients ($G_x$, $G_y$, and $G_z$) vary according to the particular localization method being used. Tailored RF pulses may be used to localize the excitations.

The control system 104 includes a workstation 110 having one or more output interfaces (e.g., display) 112 and one or more input interfaces (e.g., keyboard) 114. The workstation 110 includes a processor 116, which may be a commercially available, programmable machine running a commercially available operating system. The workstation 110 provides an operator interface that enables scan sequences to be entered into or otherwise defined for the control system 104 and the MRI system 100. The workstation 110 may be coupled to a number of servers, including, in this example, a pulse sequence server 118, a data acquisition server 120, a data processing server 122, and a data store server 124. The workstation 110 and the servers 118, 120, 122 and 124 may communicate with each other via any desired communication technique, protocol, or standard. The servers 118, 120, 122, and 124 may correspond with respective services provided by a single workstation, such as the workstation 110. The components of the control system 104 may be coupled to one another via a data bus or network (not shown) and need not be connected via respective, dedicated communication lines as shown. Any one or more of the components of the control system 104 may be implemented as a service unit, module, or other unit implemented by a common physical machine or other device, such as the workstation 110. Additional, different, or fewer components may be provided, such as combining two or more servers or providing the workstation functionality on a server or vice versa.

The pulse sequence server 118 functions in response to instructions downloaded from the workstation 110 to operate a gradient system 126 and a radio frequency ("RF") system 128. Scan sequences containing data indicative of the RF pulses and gradients may be stored in a library or other memory of the pulse sequence server 118 or other component of the control system 104. Gradient waveforms to perform the prescribed scan are produced and applied to the gradient system 126 that excites gradient coils in a gradient coil assembly 130 to produce the magnetic field gradients $G_x$, $G_y$, and $G_z$ used for position-encoding MR signals. The gradient coil assembly 130 forms part of a magnet assembly 132 that includes an annular or other polarizing magnet 134 and a whole-body RF coil array 136. In some cases, the whole-body RF coil array 136 is constructed in the form of a so-called birdcage antenna. The RF coil array 136 may have a number of individual antenna rods that run parallel to the patient tunnel and are uniformly distributed in a circumferential arrangement around the patient tunnel. The individual antenna rods may be capacitively coupled to one another in a ring shape at one end of the birdcage antenna. Other antenna or coil configurations may be used.

RF excitation waveforms are applied to the RF coil array 136 by the RF system 128 to perform a selected magnetic resonance pulse sequence. Responsive MR signals detected by the RF coil array 136 or a separate local coil array (not shown) are received by the RF system 128, amplified, demodulated, filtered and digitized under direction of the pulse sequence server 118.

The RF system 128 includes an RF transmitter for producing a wide variety of RF pulses used in MR pulse sequences. The RF transmitter is responsive to the selected scan sequence and direction from the pulse sequence server 118 to produce RF pulses of the desired frequency, phase and pulse amplitude waveform. The generated RF pulses may be applied to the whole body RF coil array 136 or to one or more local coils or coil arrays. As described below, the RF transmitter includes a plurality of transmission channels to produce RF pulses formed via the superimposition of the RF pulses generated by each transmission channel.

The RF system 128 also includes a plurality of RF receiver channels. Each RF receiver channel includes an RF amplifier that amplifies the MR signal received by the coil to which it is connected. Each receiver may also include a detector that collects and digitizes in-phase (I) and quadrature (Q) components of the received MR signal.

The pulse sequence server 118 may receive patient data from a physiological acquisition controller 138. The controller 138 receives signals from a number of different sensors connected to, or otherwise monitoring, the patient. In some cases, the sensor signals include electrocardiography (ECG) signals (via ECG electrodes) and/or respiratory signals, e.g., from a bellows. The sensor signals may be indirectly or directly indicative of patient motion. The sensor signals may be used to bin, timestamp, and/or otherwise characterize MR data as described below. The sensor signals may alternatively or additionally be used by the pulse sequence server 118 to synchronize, or "gate", the implementation of the scan sequence with the subject's respiration or heart beat.

The pulse sequence server 118 may also be in communication with a scan room interface circuit 140. The scan room interface circuit 140 may receive signals from various sensors in the scan room. The sensors may provide information indicative of the condition of the patient and/or the MRI scanner 102 (e.g., the magnet system). A subject positioning system 142 may receive commands via the scan room interface circuit 140 to move the patient to desired positions during the scan sequence. The subject positioning system 142 may direct one or more motors (not shown) that drive a bed and, thus, the subject, to a desired position.

The digitized MR signal samples produced by the RF system 128 are received by the data acquisition server 120. The data acquisition server 120 operates in response to instructions downloaded from the workstation 110 to receive the real-time MR data and provide buffer storage such that no data is lost by data overrun. In some scan sequences, the data acquisition server 120 passes the acquired MR data to the data processing server 122. However, in scans that require information derived from acquired MR data to control the further performance of the scan, the data acquisition server 120 may also be configured to produce such information and convey the information to the pulse sequence server 118. For example, during calibration or other pre-scans, MR data is acquired and used to calibrate the pulse sequence performed by the pulse sequence server 118. The calibration data may be stored in a memory or storage device or other unit of, associated with, or in communication with, any of the aforementioned servers or other devices. Also, navigator signals may be acquired during a scan and used to adjust RF or gradient system operating parameters or to control the view order in which the k-space is sampled. The data acquisition server 120 may be employed to process MR signals used to detect the arrival of contrast agent in a magnetic resonance angiography (MRA) scan. In all these examples, the data acquisition server 120 acquires MR data and processes the MR data in real-time to produce further information then used to control the scan.

The data processing server 122 receives raw k-space MR scan data from the data acquisition server 120 and processes the scan data in accordance with instructions downloaded from the workstation 110. The raw data acquired by an MR scanner are the Fourier coefficients of the image, or the so-called k-space data. The k-space data is acquired by a series of phase or frequency encodings. Each phase encoding covers a given amount of k-space data, which is related to the trajectory and sampling of the scan. The k-space reflects the sampling pattern, e.g., Cartesian or radial sampling, of the scan. For example, with Cartesian sampling, a total of 256 frequency encodings are used to generate the full k-space of one 256×256 pixel image.

Images reconstructed by the data processing server 122 are conveyed back to the workstation 110 for storage and/or display. Real-time images may be stored in a database memory cache (not shown) from which they may be output to the display 112 or an auxiliary terminal or console 144, which may be located near the magnet assembly 132 for use by attending radiologists or other operators. Batch mode images or selected real time images are stored in a database on mass storage device 146, which may include any desired storage medium. When such images have been reconstructed and transferred to storage, the data processing server 122 notifies the data store server 124 on the workstation 110. The workstation 110 may be used by an operator to archive the images, produce films, or send the images via a network to other facilities.

Figure 13:
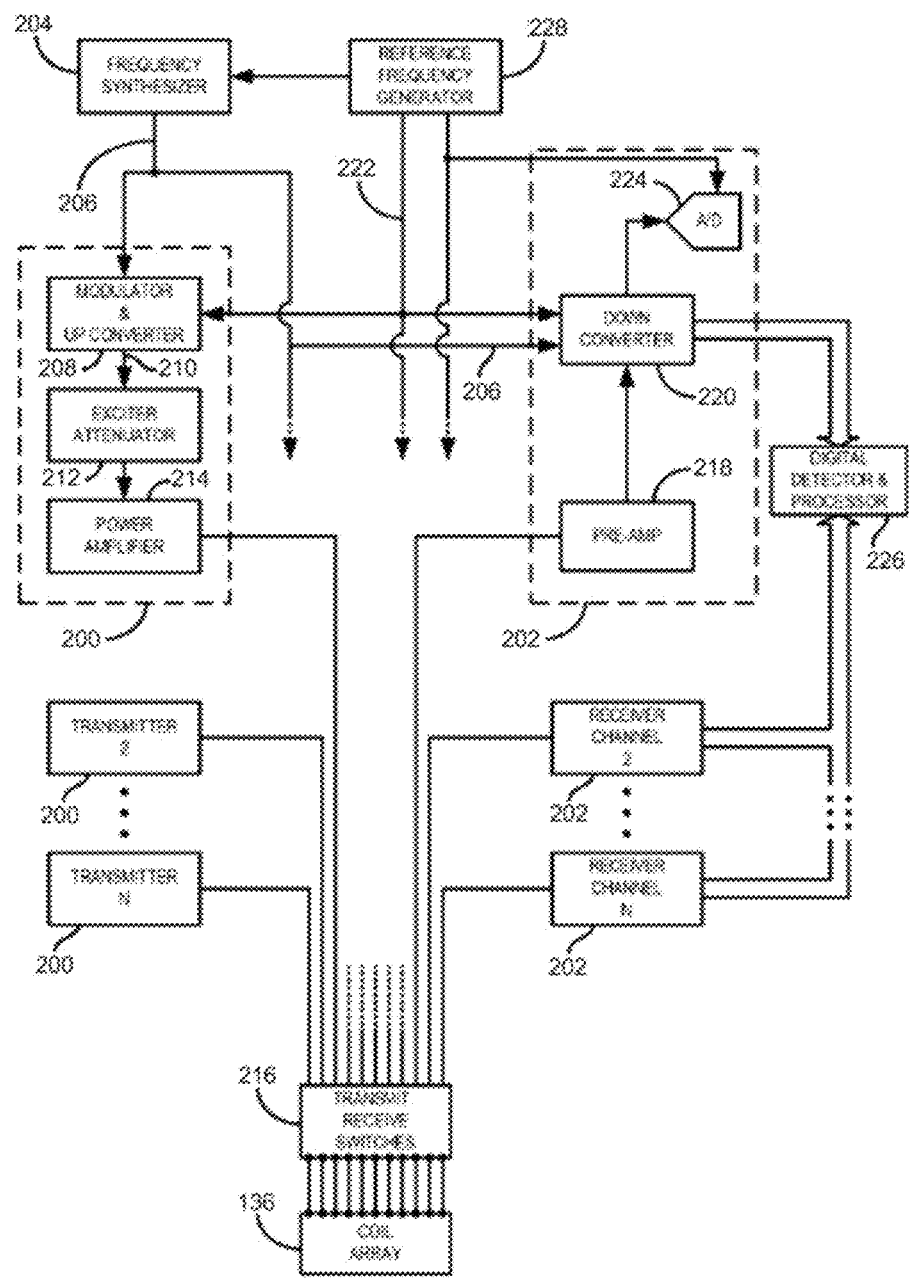
FIG. 13 is a block diagram of an RF system and other components of the MRI system of FIG. 12 for a parallel transmission architecture of the RF system in accordance with one embodiment.

Referring now to FIG. 13, the RF system 128 and other components of the system 100 are shown in greater detail. The whole body coil array 136 generally includes a plurality of coils or coil elements that may be separately driven by a plurality of RF transmitters 200 to produce a desired RF field-of-excitation. Each RF transmitter 200 forms one of the array of channels that, when superimposed, collectively define the composite RF signal. The coil array 136 may also be used with a plurality of receive channels 202. Alternatively or additionally, another whole body RF coil array (not shown) or another local RF coil may be used to acquire the MR signals. A variety of different coil array structures may be used as part of the system 100 (FIG. 12).

The RF system 126 includes a set of transmitters 200, each of which produces an individual, selected RF excitation field. The base, or carrier, frequency of the RF excitation field is produced under control of a frequency synthesizer 204, which receives a set of digital control signals from the pulse sequence server 118. These control signals may include data representative of the frequency and phase of the RF carrier signal, which may be produced at an output 206. The RF carrier is applied to a modulator and up converter 208 in each transmitter 200, where the amplitude of the RF carrier is modulated in response to a signal also received from the pulse sequence server 118. The signal defines the envelope of the RF excitation pulse to be produced and is generated by sequentially reading out a series of stored digital values. These stored digital values may be changed to enable any desired RF pulse envelope to be produced by each transmitter 200.

The magnitude of the RF excitation pulse produced at an output 210 is attenuated by an exciter attenuator circuit 212 in each transmitter 200. Each attenuator circuit 212 receives a digital command from the pulse sequence server 118. The attenuated RF excitation pulses are applied to a power amplifier 214 in each transmitter 200. The power amplifiers 214 are current source devices that connect to respective transmit inputs on a set of transmit/receive switches 216. In this example, a desired number N of the transmitters 200 are employed and connected through a corresponding number N of the transmit/receive switches 216 to a corresponding number N of the coil elements in the RF coil array 136. Other transmit/receive arrangements may be used.

The signal produced by the subject is picked up by the coil array 200 and applied to the inputs of the set of receive channels 202. A pre-amplifier 218 in each receiver channel 202 amplifies the signal by an amount determined by a digital attenuation signal received from the pulse sequence server 118 (FIG. 12). The received signal is at or around the Larmor frequency, and this high frequency signal is down converted in a two-step process by a down converter 220, which first mixes the nuclear magnetic resonance (NMR) signal with the carrier signal on the line 206, and then mixes the resulting difference signal with a reference signal on a line 222. The down converted NMR signal is applied to the input of an analog-to-digital ("A/D") converter 224 which samples and digitizes the analog signal and applies the digital signal to a digital detector and signal processor 226. The digital detector and signal processor 226 produces 16-bit in-phase (I) values and 16-bit quadrature (Q) values corresponding to the received signal, but other formats may be used. The resulting stream of digitized I and Q values of the received signal are output to the data acquisition server 120 (FIG. 12). The reference signal as well as the sampling signal applied to the A/D converter 224 are produced by a reference frequency generator 228.

The transmit/receive switches 216 are controlled and directed by the pulse sequence server 118 (FIG. 12) to connect the N transmitters 200 to the N coil elements in the coil array 136 during those parts of the pulse sequence in which an RF field is to be produced. Each transmitter 200 is separately controlled by the pulse sequence server 118 (FIG. 12) to produce an RF field of a desired amplitude, frequency, phase, and envelope at each of the N coil elements. The combined RF fields of the N coil elements produce the prescribed $B_1$ field throughout the region of interest in the subject during the imaging phase of the procedure.

When the $B_1$ field is not produced, the pulse sequence server 118 directs the transmit/receive switches 216 to connect each of the N receive channels to the respective N coil elements. Signals produced by the excited spins in the subject are picked up and separately processed as described above.

Various embodiments described herein can be used alone or in combination with one another. The foregoing detailed description has described only a few of the many possible implementations of the present invention. For this reason, this detailed description is intended by way of illustration, and not by way of limitation.

The invention claimed is:

1. A method of three-dimensional (3D), cine, magnetic resonance (MR) imaging of a volume undergoing repetitive motion, the method comprising:
   obtaining source MR slice data indicative of a plurality of source slices of the volume during the repetitive motion;
   obtaining anchor MR slice data indicative of an anchor slice of the volume during the repetitive motion, the anchor slice intersecting the plurality of source slices;
   reconstructing, with a processor, the source MR slice data and the anchor MR slice data; and
   generating, with the processor, for each phase of the repetitive motion, volume data based on a respective subset of the reconstructed source MR slice data;
   wherein, for each phase of the repetitive motion, generating the volume data comprises:
     selecting the respective subset of slices of the plurality of source slices based on a correlation of the reconstructed source MR slice data and the reconstructed anchor MR slice data along a respective intersection between each source slice of the plurality of source slices and the anchor slice; and
     correcting the reconstructed source MR slice data of the selected subset of source slices for misalignment with the reconstructed anchor MR slice data.

2. The method of claim 1, wherein obtaining the anchor MR slice data comprises acquiring anchor slice data indicative of a plurality of anchor slices of the volume, each anchor slice of the plurality of anchor slices intersecting the plurality of source slices.

3. The method of claim 2, wherein generating the volume data further comprises:
   computing the correlation of the source MR slice data along the intersection with the plurality of anchor slices; and
   selecting an anchor slice of the plurality of anchor slices based on the computed correlation.

4. The method of claim 2, wherein the plurality of anchor slices are disposed at different rotation angles around an axis that intersects the plurality of source slices.

5. The method of claim 2, wherein generating the volume data further comprises:
   computing a correlation score between each anchor slice of the plurality of anchor slices and each source slice of the plurality of source slices;
   determining a set of source slices of the plurality of source slices at which the correlation score reaches a local maximum; and
   determining the anchor slice of the plurality of anchor slices for which the set of source slices is most consistent across all phases of the repetitive motion.

6. The method of claim 5, wherein generating the volume data further comprises:
   computing an anchor correlation score between the determined anchor slice and each other anchor slice of the plurality of anchor slices;
   selecting a further anchor slice of the plurality of anchor slices to be used in selecting the respective subset of source slices, the further anchor slice having a maximum score of the computed anchor correlation scores.

7. The method of claim 1, further comprising obtaining time stamp data for the source MR slice data and the anchor MR slice data.

8. The method of claim 7, further comprising normalizing the source MR slice data based on the time stamp data to assign the source MR slice data and the anchor MR slice data to a respective phase of the repetitive motion.

9. The method of claim 1, wherein generating the volume data further comprises interpolating the corrected source MR slice data of the selected subset of source slices to generate further volume data.

10. The method of claim 1, wherein correcting the selected subset of source slices comprises selecting a key volume as a reference to be used in a non-rigid registration.

11. The method of claim 1, wherein each source slice of the plurality of source slices is orthogonal to the anchor slice and arranged in a source slice stack.

12. The method of claim 1, wherein obtaining the source MR slice data comprises implementing an acquisition protocol in which the plurality of source slices are contiguously scanned as a group without intermediate scans for the anchor MR slice data.

13. A computer program product for implementing a method of three-dimensional (3D), cine magnetic resonance (MR) image reconstruction of a volume undergoing repetitive motion, the computer program product comprising one or more computer-readable storage media having stored thereon instructions executable by one or more processors of a computing system to cause the computing system to perform operations comprising:
   obtaining source MR slice data indicative of a stack of source slices of the volume during the repetitive motion;
   obtaining anchor MR slice data indicative of a plurality of anchor slices of the volume during the repetitive motion, each anchor slice of the plurality of anchor slices intersecting the stack;
   reconstructing the source MR slice data and the anchor MR slice data; and
   implementing a 3D image assembly procedure to reconstruct, for each phase of the repetitive motion, volume data based on a respective subset of the reconstructed source MR slice data;
   wherein implementing the 3D image assembly procedure comprises:
      selecting an anchor slice of a plurality of anchor slices;
      selecting, for each phase of the repetitive motion, the respective subset of source slices based on a correlation of the reconstructed anchor MR slice data of the selected anchor slice and the source MR slice data of each source slice of the stack along an intersection of the selected anchor slice and the respective source slice of the stack; and
      correcting the reconstructed source MR slice data of the selected subset of source slices for misalignment of the reconstructed source MR slice data with the reconstructed anchor MR slice data.

14. The computer program product of claim 13, wherein the operations further comprise obtaining time stamp data for the source MR slice data and the anchor MR slice data.

15. The computer program product of claim 14, wherein the operations further comprise normalizing the source MR slice data based on the time stamp data to assign the source MR slice data and the anchor MR slice data to a respective phase of the repetitive motion.

16. The computer program product of claim 14, wherein obtaining the anchor MR slice data comprises implementing an acquisition protocol in which the plurality of anchor slices are contiguously scanned as a group without intermediate scans for the source MR slice data.

17. The computer program product of claim 13, wherein selecting the anchor slice is repeated for each phase of the repetitive motion.

18. A data processing system for a magnetic resonance imaging (MRI) system, the data processing system comprising:
   a data store in which source MR slice data and anchor slice data are stored, wherein:
      the source MR slice data is indicative of a plurality of source slices of the volume during the repetitive motion,
      the anchor MR slice data is indicative of an anchor slice of the volume during the repetitive motion, and
      the anchor slice intersects the plurality of source slices;
   a processor coupled to the data store, and configured to reconstruct, for each phase of the repetitive motion, volume data based on a respective subset of the source MR slice data;
   wherein the processor is further configured to select the anchor slice from a plurality of anchor MR slices;
   wherein the processor is further configured to, for each phase of the repetitive motion, select the respective subset of source slices having a maximum correlation between the source MR slice data and the anchor MR slice data along a respective intersection between each source slice of the plurality of source slices and the anchor slice; and
   wherein the processor is further configured to, for each phase of the repetitive motion, correct the source MR slice data of the selected subset of source slices for misalignment with the anchor MR slice data.

19. The data processing system of claim 18, wherein the processor is further configured to normalize the source MR slice data via interpolation of the source MR slice data for consecutively acquired source slices of the plurality of source slices based on time stamp data for the source MR slice data such the adjusted source MR slice data is indicative of a respective phase of the repetitive motion.

20. The data processing system of claim 18, wherein the processor is configured to repeat selection of the anchor slice from the plurality of anchor MR slices for each phase of the repetitive motion.

* * * * *